US011000328B2

(12) United States Patent
Batchelor et al.

(10) Patent No.: US 11,000,328 B2
(45) Date of Patent: May 11, 2021

(54) RESISTIVELY HEATED ELECTROSURGICAL DEVICE

(71) Applicant: GYRUS ACMI, INC., Southborough, MA (US)

(72) Inventors: Kester J. Batchelor, Mound, MN (US); Richard J. Curtis, Corcoran, MN (US); John Mensch, Plymouth, MN (US); Jyue Boon Lim, New Brighton, MN (US); Riyad Moe, Madison, WI (US)

(73) Assignee: Gyrus Acmi, Inc., Southborough, MA (US)

( * ) Notice: Subject to any disclaimer, the term of this patent is extended or adjusted under 35 U.S.C. 154(b) by 478 days.

(21) Appl. No.: 15/797,014

(22) Filed: Oct. 30, 2017

(65) Prior Publication Data

US 2018/0125562 A1 May 10, 2018

Related U.S. Application Data

(60) Provisional application No. 62/419,610, filed on Nov. 9, 2016.

(51) Int. Cl.
*A61B 18/10* (2006.01)
*A61B 18/08* (2006.01)
(Continued)

(52) U.S. Cl.
CPC .............. *A61B 18/10* (2013.01); *A61B 18/08* (2013.01); *A61B 18/085* (2013.01);
(Continued)

(58) Field of Classification Search
None
See application file for complete search history.

(56) References Cited

U.S. PATENT DOCUMENTS

| 4,196,734 A | 4/1980 | Harris |
| 4,493,320 A | 1/1985 | Treat |

(Continued)

FOREIGN PATENT DOCUMENTS

| DE | 3215055 A1 | 10/1983 |
| EP | 1878399 A1 | 1/2008 |

(Continued)

OTHER PUBLICATIONS

Japanese Office Action for Japanese Application. No. 2016-567389, dated Sep. 5, 2017.

(Continued)

*Primary Examiner* — Linda C Dvorak
*Assistant Examiner* — Bo Ouyang
(74) *Attorney, Agent, or Firm* — Schwegman Lundberg & Woessner, P.A.

(57) ABSTRACT

A medical device includes a hand piece, a heating power supply, and a therapy power supply. The hand piece includes a first electrode including a heater. The heating power supply selectively provides heating power to the heater. The therapy power supply selectively provides therapeutic power to the first electrode. The medical device is changeable between operating a first electrosurgical configuration and a second electrosurgical configuration. In the first electrosurgical configuration, the heating power supply provides the heating power to the heater to heat the first electrode and the therapy power supply provides the therapeutic power to the first electrode. A single conductor line carries the heating power to the heater and the therapeutic power to the first electrode.

13 Claims, 12 Drawing Sheets

(51) Int. Cl.
    *A61B 18/14*     (2006.01)
    *A61B 18/00*     (2006.01)
    *A61B 90/00*     (2016.01)
    *A61B 18/12*     (2006.01)

(52) U.S. Cl.
    CPC ...... *A61B 18/1442* (2013.01); *A61B 18/1482* (2013.01); *A61B 18/149* (2013.01); *A61B 2018/00178* (2013.01); *A61B 2018/00654* (2013.01); *A61B 2018/00916* (2013.01); *A61B 2018/00958* (2013.01); *A61B 2018/00994* (2013.01); *A61B 2018/126* (2013.01); *A61B 2018/1253* (2013.01); *A61B 2018/1273* (2013.01); *A61B 2018/141* (2013.01); *A61B 2018/1412* (2013.01); *A61B 2018/1422* (2013.01); *A61B 2018/1462* (2013.01); *A61B 2018/1475* (2013.01); *A61B 2090/0817* (2016.02)

(56) References Cited

U.S. PATENT DOCUMENTS

| | | | |
|---|---|---|---|
| 4,905,691 | A | 3/1990 | Rydell |
| 5,250,046 | A | 10/1993 | Lee |
| 5,807,392 | A | 9/1998 | Eggers |
| 6,221,039 | B1 | 4/2001 | Durgin et al. |
| 6,235,027 | B1 | 5/2001 | Herzon |
| 6,471,701 | B2 | 10/2002 | Brommersma |
| 6,533,778 | B2 | 3/2003 | Herzon |
| 6,610,056 | B2 | 8/2003 | Durgin |
| 6,827,717 | B2 | 12/2004 | Brommersma |
| 7,211,079 | B2 | 5/2007 | Treat |
| 7,276,068 | B2 | 10/2007 | Johnson et al. |
| 7,326,202 | B2 | 2/2008 | McGraffigan |
| 7,922,713 | B2 | 4/2011 | Geisel |
| 8,382,748 | B2 | 2/2013 | Geisel |
| 8,430,870 | B2 | 4/2013 | Manwaring et al. |
| 8,435,237 | B2 | 5/2013 | Bahney |
| 8,491,578 | B2 | 7/2013 | Manwaring et al. |
| 9,402,679 | B2 | 8/2016 | Ginnebaugh et al. |
| 2003/0040744 | A1 | 2/2003 | Latterell et al. |
| 2003/0130658 | A1 | 7/2003 | Goble et al. |
| 2007/0156137 | A1 | 7/2007 | Geisel |
| 2008/0015575 | A1 | 1/2008 | Odom et al. |
| 2009/0248002 | A1* | 10/2009 | Takashino .......... A61B 18/1442 606/28 |
| 2010/0268211 | A1 | 10/2010 | Manwaring et al. |
| 2010/0331621 | A1 | 12/2010 | St. George et al. |
| 2011/0077629 | A1 | 3/2011 | Tanaka et al. |
| 2012/0296325 | A1 | 11/2012 | Takashino |
| 2014/0276786 | A1 | 9/2014 | Batchelor |
| 2014/0276795 | A1* | 9/2014 | Batchelor .......... A61B 18/1445 606/42 |
| 2014/0276796 | A1 | 9/2014 | Batchelor et al. |
| 2014/0276797 | A1 | 9/2014 | Batchelor et al. |
| 2014/0276804 | A1 | 9/2014 | Batchelor |
| 2014/0364866 | A1 | 12/2014 | Dryden et al. |
| 2015/0030135 | A1 | 1/2015 | Choi et al. |
| 2015/0032094 | A1* | 1/2015 | Kane .................. A61B 18/10 606/33 |
| 2015/0320485 | A1* | 11/2015 | Batchelor .......... A61B 18/1442 606/41 |

FOREIGN PATENT DOCUMENTS

| | | |
|---|---|---|
| EP | 2491880 A1 | 8/2012 |
| EP | 2848224 A2 | 3/2015 |
| JP | 2008-023335 A | 2/2008 |
| JP | 2009-247893 A | 10/2009 |
| WO | 2011/064881 A1 | 4/2013 |
| WO | 2013/103934 A1 | 7/2013 |

OTHER PUBLICATIONS

Non-Final Office Action for U.S. Appl. No. 14/708,836 dated Dec. 20, 2017.
Potentially related U.S. Appl. No. 14/708,836, filed May 11, 2015.
Potentially related patent application PCT/US2015/30135; filed on May 11, 2015.
Written Opinion of the International Preliminary Examining Authority for International Application No. PCT/US2015/030135, dated Sep. 8, 2016.
International Preliminary Report on Patentability for International Application No. PCT/US2015/030135, dated Oct. 27, 2016.
International Search Report and Written Opinion for International Application No. PCT/US2015/030135, dated Nov. 6, 2015.

* cited by examiner

RESISTIVELY HEATED ELECTROSURGICAL DEVICE

FIELD

The present teachings relate to a medical device, and more particularly to an electrosurgical medical device that combines thermal, therapeutic, and mechanical modalities.

BACKGROUND

Electrosurgical medical devices generally fall into one of two categories: monopolar medical devices and bipolar medical devices.

A monopolar medical device includes an active electrode electrically connected to an electrosurgical generator. A return electrode, typically in the form of a patient pad, is also electrically connected to the electrosurgical generator and can be placed in contact with a patient. In use, electrical current is passed from the electrosurgical generator to the active electrode, through a site or a region of the patient's anatomy (i.e., a tissue or a vessel) to the patient pad, and back to the electrosurgical generator.

A bipolar medical device includes an active electrode and a return electrode adjacent the active electrode, both of which are electrically connected to an electrosurgical generator. In use, a site or a region of the anatomy is placed between the active and return electrodes, and electrical current passes from the electrosurgical generator to the active electrode, through the site or a region of the anatomy to the adjacent return electrode, and then back to the electrosurgical generator.

Examples of electrosurgical medical devices may be found in U.S. Pat. Nos. 4,196,734; 5,807,392; 7,211,079; 7,276,068; 7,922,713; 8,382,748; 8,491,578 and U.S. Patent Application Publication No. 2010/0331621 all of which are incorporated by reference herein in their entirety for all purposes.

While both monopolar and bipolar medical devices are desirable for use in various medical procedures, both have inherent shortcomings, however. For example, monopolar medical devices are known to pass relatively high electrical currents through the patient, which any cause unwanted tissue and/or organ damage. Moreover, some procedures cannot allow the use of monopolar medical devices because of high thermal spread and dispersed energy format. While bipolar medical devices minimize these shortcomings, accurately controlling which electrode is the active electrode is difficult.

It would therefore be desirable to have a medical device that can address at least one of the aforementioned shortcomings. For example, it would be attractive to have a single electrosurgical medical device that can be used in both monopolar and bipolar modes. It would be desirable to have an electrosurgical medical device that can be quickly switch between a monopolar mode and a bipolar mode. It would be advantageous to have medical device that can be used in a variety of arrangements in each mode. It would be attractive to have an electrosurgical medical device that uses less power and voltage, and therefore less current to perform a device function. It would be attractive to have an electrosurgical medical device with a plurality of electrodes, in which one or more of the electrodes are resistively heated to allow for thermionic disassociation of the electrons, ions, or both so that electrons, ions, or both in a field are accelerated. In this regard, it would be desirable because less voltage may be required to get the same disassociation of the electrons, ions, or both than with only voltage.

SUMMARY

The present teachings provide a medical device that addresses at least one of the aforementioned shortcomings. For example, the teachings herein provide a single electrosurgical medical device that can be used in both monopolar and bipolar modes. The teachings herein also provide an electrosurgical medical device that can be quickly switch between a monopolar mode and a bipolar mode. The electrosurgical medical device according to the present teachings provide a device that uses less power and voltage, and therefore less current to perform a device function. In each mode, the medical device according to the teachings herein can be used in a variety of arrangements. The teachings herein provide an electrosurgical medical device with a plurality of electrodes, in which one or more of the electrodes are resistively heated to allow for thermionic disassociation of the electrons, ions, or both so that electrons, ions, or both in a field are accelerated. In this regard, the present teachings require less voltage to get the same disassociation of the electrons, ions, or both than with only voltage.

The present teachings provide a medical device that includes a hand piece, a heating power supply, and a therapy power supply. The hand piece includes a first electrode including a heater. The heating power supply selectively provides heating power to the heater. The therapy power supply selectively provides therapeutic power to the first electrode. The medical device is changeable between operating a first electrosurgical configuration and a second electrosurgical configuration. In the first electrosurgical configuration, the heating power supply provides the heating power to the heater to heat the first electrode and the therapy power supply provides the therapeutic power to the first electrode.

The present teachings also provide a medical device, comprising a hand piece, a heating power supply, and a therapy power supply. The hand piece comprises a first electrode including a heater, a second electrode, and a third electrode. The heating power supply selectively supplies heating power to the heater. The therapy power supply selectively provides therapeutic power to the first, second, and/or third electrodes. The medical device is selectively changeable between a first electrosurgical configuration and a second electrosurgical configuration. In the first electrosurgical configuration, the heating power supply provides the heating power the heater to heat the first electrode and the therapy power supply provides the therapeutic power to the first electrode.

DETAILED DESCRIPTION

Figure 1A:
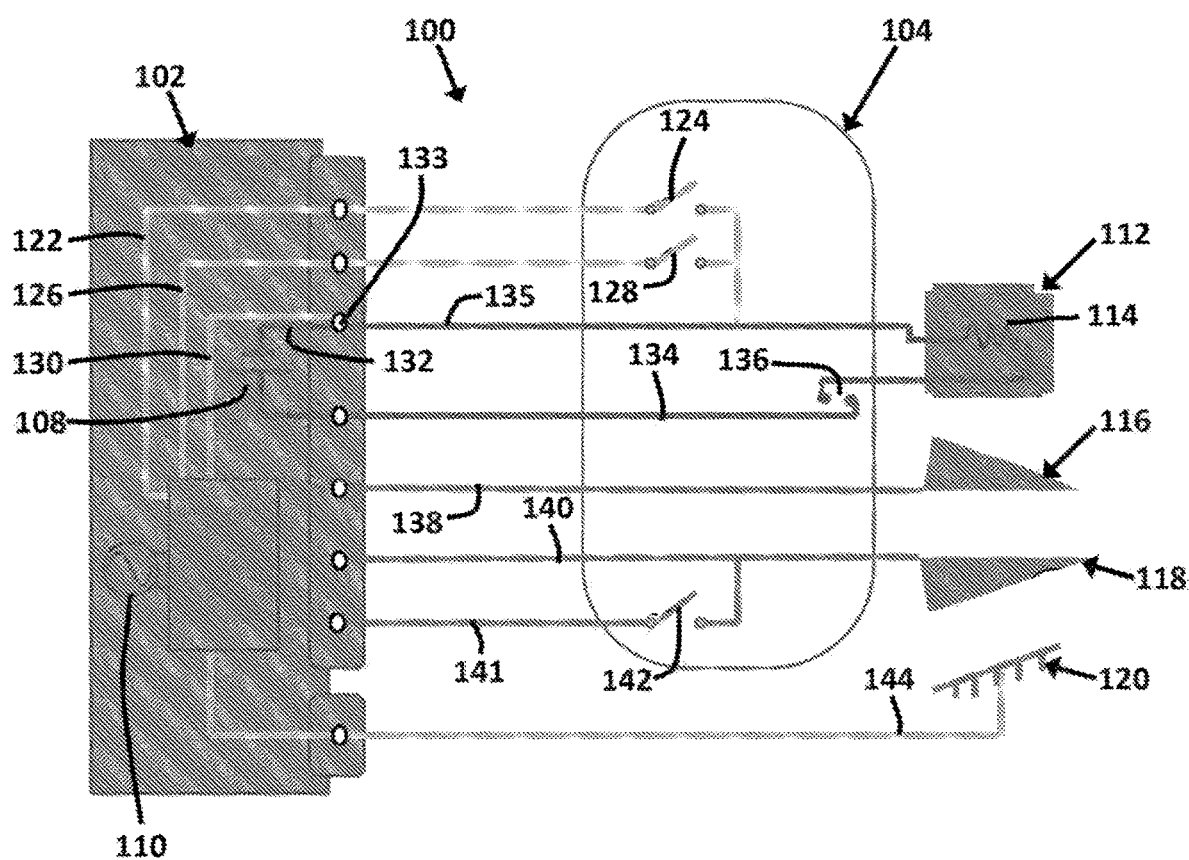
FIG. 1a is a schematic circuit of a medical device.

This application claims the benefit of U.S. 62/419,610 filed on Nov. 9, 2016, the entire disclosure of which is hereby incorporated by reference herein for all purposes.

The present teachings relate to a medical device. More specifically, the present teachings relate to a medical device and associated components of an electrosurgical medical device. The teachings herein can be applied to any medical device. For example, the medical device may be forceps, scissors, scalpels, spatulas, J-hooks, gaspers, snares, resectoscopes, tweezers, the like, or a combination thereof.

The one or more electrosurgical medical devices can be used in one or more arrangements, configurations or modes (i.e., monopolar, bipolar, or both). The electrosurgical medical device may combine one or more thermal, electrosurgical or therapeutic, and mechanical modalities.

The electrosurgical medical device may be used in electro surgery. The electrosurgical medical device can be used in any medical procedure to perform any device function. For example, the medical procedure rimy be any invasive procedure, minimally invasive procedure, or both. Some non-limiting device functions may include effecting hemostasis; coagulating blood; gasping, manipulating, cutting, transecting, sealing, cauterizing desiccating, ablating, welding, fulgurating, vaporizing, and/or otherwise effecting an object or any area of the anatomy such as tissue or a vessel.

The electrosurgical medical device can be selectively switched between at least two electrosurgical operating configurations. That is, the electrosurgical medical device can be switched between a first electrosurgical operating configuration and a second electrosurgical operating configuration. In each electrosurgical operating configuration, the electrosurgical medical device can be used in a variety of arrangements and modes. For example, in each operating arrangement or configuration, the electrosurgical medical device can be used in one or more monopolar modes and one or more bipolar modes. The electrosurgical medical device of the present teachings can be easily switched between the various operating arrangements, configurations and modes. More specifically, a surgeon can advantageously switch between operating arrangements, configurations and modes before or during a medical procedure without changing devices, without needing a second hand, without disrupting and/or prolonging the medical procedure, or a combination thereof. Such "switchable" electrosurgical medical devices may include an electrosurgical blade, or they may include other features, which may form a medical device that does not include a blade. For example, such "switchable" medical devices may be forceps, tweezers, segments of a medical spatula or J-hook, a snare, resectoscope, etc. The electrosurgical medical device may also operate in a single mode that is, the electrosurgical device may not be switchable between at least two electrosurgical operating conditions like in the aforementioned examples. Such "non-switchable" electrosurgical medical devices may include an electrosurgical blade, or they may include other features, which may form a medical device that does not include a blade. For example, such medical devices may be forceps, tweezers, segments of a medical spatula or J-hook, a snare, resectoscope, etc.

The electrosurgical medical device may include a hand piece. The hand piece may function to provide a gripping or grasping area for handling the electrosurgical medical device. The hand piece may include one or more controls for operating the electrosurgical medical device. The one or more controls may function to control, move, extend, retract, and/or manipulate one or more functional features and/or the one or more extensions to perform a device function during a medical procedure. The one or more controls may also control communication of power and/or signals between the one or more generators and the electrosurgical medical device. That is, in use, the one or more controls may control the type and/or the amount of power, the type and/or the amount or number of signals, or both that are communicated between the one or more generators and the electrosurgical medical device. In other words, the one or more controls may control whether monopolar or bipolar power is communicated between the generator to the electrosurgical medical device; whether heating power, RF power, or both is communicated between the generator to the electrosurgical medical device; and/or which of the one or more electrodes the power and/or signals are communicated to. Moreover, the one or more controls may control the particular operating arrangement, configuration and/or mode in which the electrosurgical medical device is used.

The one or more controls may include one or more knobs, switches, slides, buttons, etc. The hand piece may include one or more connections (i.e., plug, ports, chords, etc.) for connecting the electrosurgical medical device to one or more generators, to one or more auxiliary devices, or both.

The electrosurgical medical device may include one or more extensions. The one or more extensions may be used to perform a device function in any medical procedure. For example, the one or more extensions may assist effecting hemostasis; coagulating blood; grasping, manipulating, cutting, transecting, sealing, cauterizing, desiccating, ablating, welding, fulgurating, vaporizing, and/or otherwise effecting an object or any area of the anatomy such as tissue or a vessel. The one or more extensions may function to grip, hold, squeeze, manipulate, handle, and/or move any object. The electrosurgical medical device may comprise any number of extensions. For example, the electrosurgical medical device may comprise one or more extensions, two or more extensions, preferably three or more extensions, or even four or more extensions. The electrosurgical medical device may have preferably three of less extensions, two or less extensions, or even one extension.

The one or more extensions may be moveable or immoveable. For example, one or more extensions may be moveable, while one or more extensions may be immobilized. The one or more extensions may be moved or otherwise manipulated vita one or more controls on the hand piece, one or more controls at a remote location (i.e., a foot pedal, a remote computer, etc.), or both. The one or nine extensions may be moved in any way or direction to perform a device function. For example, one or more extensions may be advanced, extended, retracted, opened, closed, pivoted, rotated, articulated, actuated, reciprocated, clamped, the like, or a combination thereof. The one or inure extensions may be axially moved, longitudinally moved, moved along an arc, or a combination thereof. The one or more extensions may be moved individually, together in unison, sequentially, or a combination thereof. The one or more extensions may be moveable or immovable so that the electrosurgical medical device can be used as any medical device to perform a device function.

The one or more extensions may firm one or more portions or segments of an arm, jaw, blade, scalpel, or portions of any medical device, such as a snare, forceps, scissors, scalpels, spatulas, J-hooks, graspers, resectoscopes, tweezers, the like, the combination of. One extension may be a center extension, which may be adjacent or sandwiched between two outer extensions (i.e., arranged as a spatula, J-hook, etc.) The one or more extensions may function as a blade, a blade electrode, or both. The one or more blades, blade electrodes, or both may be advanced beyond a distal end of one or more extensions to cut or transect a pan of the anatomy, such as a vessel or tissue. The one or more blades, blade electrodes, or both may be advanced beyond a distal end of the one or more extensions to cauterize a vessel or tissue or coagulate blood. One or more extensions may move or pivot so that that a vessel, tissue, or object can be gripped, grasped, squeezed, manipulated, sealed, held, moved, and/or otherwise gripped.

The one or more extensions may comprise or be fabricated from any material. Preferably, the one or more extensions are fabricated from any material that is safe for use in an electrosurgical procedure. For example, the one or more extensions may be fabricated from one or more metals, plastics, polymers, elastomers, gold, silver, copper, titanium, aluminum, iron based metals, stainless steel, silicone, polytetrafluoroethylene (PTFE), insulating polymers, rubber, or a combination thereof.

The one or more extensions rimy include one or more functional features that may assist in performing a device function. Exemplary and non-limiting functional features may include one or more or various teeth, serrations, mouse teeth, smooth portions, sharp edges, cutouts, notches, wires, scalpels; features or segments of a J-hook; features or segments of a Spatula; features or segments of a snare; features or segments of a forceps; features or segments of a resectoscope; the like, or a combination thereof.

The one or more functional features, extensions, or portions of the one or more functional features or extensions, or a combination thereof, may comprise one or more active portions. The one or more active portions may function to contact a portion of the anatomy to perform a device function thereon or thereto. In other words, the one or more active portions may be in communication with the one or more generators, the one or more electrodes, the one or more extensions, the one or more functional features, or a combination thereof and may function to transmit power, signals, or both to or through the anatomy.

The one or more functional features, extensions, or both may include one or more insulating portions. The one or more insulating portions may prevent accidental or inadvertent or even intentional arching or shorting between adjacent active portions, electrodes, or both. Preferably, each extension, functional feature, or a combination thereof is coated with an insulating material. The one or more extensions may be coated with an insulating material in regions where a user contacts the one or more extensions. The one or more insulating portions may comprise any insulating material. For example, the one or more insulating portions may be such silicone or polytetrafluoroethylene.

The electrosurgical medical device may include one or more electrodes. In use, electrical current, power, and/or signals can be communicated between the one or more generators and the one or more electrodes so that a device function can be performed on a site or region of the anatomy with the one or more extensions, functional features, active portions, or a combination thereof.

The one or more electrodes may be any conducting instrument, device, or probe. The one or more electrodes may be a loop electrode. The one or more electrodes, loop electrodes, or both may be a monopolar, bipolar, or both. The one or more electrodes may be fabricated from any material that is safe for use in electro surgery and suitable for performing one or more device functions. The one or more electrodes with a heater may be fabricated from any material such as Nichrome. The one or more electrodes may be in electrical communication with the one or more generators. The one or more electrodes may be in electrical communication with the one or more generators via one or more connections, which may be one or more wires. The one or more electrodes may be in communication with the one or more extensions, active portions, functional features, or a combination thereof. One electrode may be in communication with one extension. Alternatively, more thin one electrode can be in communication with a single extension. One or more insulating materials may surround the one or more electrodes to prevent accidental and/or inadvertent arching therebetween.

One or more of the electrodes may include a heater. The heater may be any feature, material, or device that may heat the one or more electrodes. The heater may be provided with electrical power, heating power, therapeutic power, one or more signals, or a combination thereof from any source to resistively heat the one or more electrodes. Preferably, the heater receives heating power from the one or more generators to heat the one or more electrodes with the heater. More preferably, the heater receives heating power from the heating power source. The heater may be, for example, a resistor, a wire, a ferromagnetic material, the like, or a combination thereof. The heating power may be constantly supplied to the heater, or the heating power may be selectively supplied to the heater to heat the one or more electrodes. The heating power can be supplied to the heater at any time. In other words, the heating power can be supplied to the heater before therapeutic power is supplied to the electrode, while therapeutic power is being supplied to the electrode, or after therapeutic power has been supplied to the electrode. The heating power can be supplied to the heater to heat the one or more electrodes before or while performing a device function. The heating power can be supplied to the heater via a constant signal, or the heating power can be pulsed, oscillated, or both. The heating power can be supplied to the heater on an "as-needed" basis to maintain the one or more heaters/electrodes at a predetermined and desired temperature; to elevate the one or more heaters/electrodes to a predetermined temperature; to allow the temperature of the one or more electrodes to drop, or a combination thereof, for example. The heating power may be controlled via the hand piece, one or more controls on the hand piece, one or more controls at a remote location (i.e., a foot pedal, a remote computer, etc.), or a combination thereof. The heater may function to provide thermal cutting.

A resistively heated electrode may advantageously allow or provide for thermionic disassociation of the electrons, ions, or both. That is, by resistively heating the one or more of the electrodes, electrons, ions, or both in an electrical field are accelerated. Thermionic disassociation may be advantageous because less voltage may be required to get the same disassociation of the electrons, ions, or both than with only voltage. In other words, a greater total energy is possible with lower voltage. Moreover, in a bipolar mode, a heated electrode is more likely to activate as an intended source of therapeutic current (i.e., the active electrode) providing the surgeon with greater control of the location of the intended tissue effect. The one or more electrodes with a heater may be heated even if the one or more electrodes, with a heater are not specifically configured or arranged to perform a device function. For example, if one or more other electrode/extension combinations are used to perform a device function (i.e., a second and third extension), the one or more electrodes with a heater (i.e., a first extension) may nonetheless still be heated. Alternatively, the one or more electrodes with a heater may be restricted from being heated in an arrangement or configuration where they are not used to perform a device function. Again, this may be controlled via the hand piece, one or more controls on the hand piece, one or more controls at a remote location (i.e., a foot pedal, a remote computer), or a combination thereof.

The electrosurgical medical device may include, or be in communication with, one or more generators. The generator may function to provide power, signals, or both to the electrosurgical medical device. The generator may function to provide power, signals, or both to the electrosurgical medical device so that the electrosurgical medical device can perform a device function. The device function(s) may include, but are not limited to, any of the examples recited above. The one or more generators may be powered by any energy source or power source. For example, the one or more generators may be powered by AC power, DC power, or a combination of AC and DC power.

The one or more generators may provide any power and/or any signal to the electrosurgical medical device. For example, the power or signal may be a therapeutic power, a heating power, an RF power, a monopolar power or signal, a bipolar power or signal, an electric signal an electric current, a voltage, an oscillating electrical energy, or a combination thereof. Preferably, both therapeutic power and heating power is provided by the one or more generators.

The one or more generators may include a heating power supply, a therapy power supply, or both. The heating power supply may supply heating power, therapeutic power, or both to the electrosurgical medical device. The therapy power supply may supply therapeutic power, heating power, or both to the electrosurgical medical device. The heating power may be the same as the therapeutic power, or may be different. The heating power may be any electrical signal that is communicated to a heater associated with one or more of the electrodes. The heating power may heat the heater and therefore resistive heat the one or more electrodes. The heating power may be an electrical current or signal that remains within the circuit and is restricted or prevented from transferring to a portion of the anatomy.

The therapeutic power may be an electrical current or signal that is communicated or transmitted to or through the anatomy to perform a device function thereon. The therapeutic power may be a monopolar signal, a bipolar signal, or both. The monopolar signal may be any signal that has a voltage differential between an active port and a return port on the generator. The monopolar signal may be any signal that when applied by the electrosurgical medical device extends from one pole of an electrode or extension to another pole located at a remote location (i.e., to the patient pad). The monopolar signal may be selectively applied by opening or closing one or more switches or controls on the hand piece; one or more switches or controls extending between the one or more generators and the one or more electrodes (i.e., a foot pad), one or more controls or switches at a remote location (i.e., a remote computer), or a combination thereof. The bipolar signal may be any signal that has a voltage differential between two electrodes connected to the electrosurgical medical device.

The one or more generators may include one or more connections. The one or more connections may be any connection, port, plug, inlet, outlet, etc. for supplying, transmitting, or communicating the power, signals, or both between the one or more generators and the electrosurgical medical device. For example, the one or more connectors may include one or more active ports and one or more return ports that may cooperate to form a closed circuit. The one or more connections may be any suitable connection, port, plug, inlet, outlet, etc. for connecting one or more conductor wires. One or more conductor wirers may extend from each of the connections on the generator. For example, a single conductor wire may extend from a single connection on the generator, or a plurality of conductor wires may extend from a single connection on the generator. A single conductor wire may connect to a single connection on the generator, and then the signal conductor wire may include a branch or split at a node so that a plurality of wires may extend from the branch of split to one or more electrodes and/or heaters.

One or more power connections or conductor wires may extend from the generator, the heating power supply, the therapy power supply, or a combination thereof to the one or more electrodes, heaters, or a combination thereof. Each of the conductor wires may be adapted to carry a single signal from the corresponding power supply to the corresponding electrode or heater. For example, a dedicated conductor wire may extend from the generator, the heating power supply, or the therapy supply to a corresponding electrode or heater and carry to the electrode or heater the corresponding heating signal or therapy signal.

Each of the conductor wires may be adapted to carry a plurality of signals. For example, a single conductor wire may extend from the generator, the heating power supply, or the therapy supply to a plurality of electrodes or heaters. The single conductor wire may be adapted to carry both a heating signal from the heating power supply and a therapy signal from the therapy power supply. The device and/or circuit may include suitable features, such as a switch, for example, to prevent both the heating power supply signal and the therapy power supply signal from being transmitted through the single conductor line at the same time. However, it is understood that the heating power supply signal and the therapy supply signal can be transmitted through the single conductor line at the same time, or one after the other in rapid succession.

The single conductor line that carries a plurality of signals from the power supplies may be connected to a corresponding connection, socket, receptacle, or plug on the generator. The connection, socket, receptacle, or plug on the generator may include a plurality of pins, each of which may be adapted to carry the corresponding signal from the corresponding power supply (heating power supply or therapy power supply) to the socket, receptacle, or plug for connecting to the single conductor line. Alternatively, the connection, socket, receptacle, or plug may include a single pin, and upstream of the sine pin may be a node or electrical branch that divides or separates the single pin into corresponding wires for connecting to each of the heating and therapeutic power supplies.

The one or more generators may include one or more controls (i.e., switches, buttons, knobs, foot pedals, etc.) so that power, signals, or both can be selectively supplied to the electrosurgical device based on a desired operating mode, arrangement, and/or configuration, for example. The one or more generators may include a central processing unit (CPU), a series of internal switching, or both. The internal switching may provide a signal from an activation circuit to the voltage source so that the voltage source can be supplied to the electrosurgical medical device. The CPU may be interchanged with the internal switching and the switching may perform the sane functions as the CPU. The CPU may be any device that supplies power, current, electrical reconfiguration; may be a switch between two or more powers (i.e., hunting power, therapeutic power, or both); a switch between two or more arrangements, modes or configurations, or a combination thereof. The CPU may be used to switch the electrosurgical medical device between one or more modes, arrangements, configurations, or a combination thereof.

One or more remote electrodes may be in electrical communication with the one or more generators, the electrosurgical medical device, or both. The one or more remote electrodes may be one or more patient pads. The one or more remote electrodes or patient pads may complete a circuit for the transfer or communication of power, signals, or both between the one or more generators and at least one of the electrodes. The one or more patient pads may be used in a monopolar operating mode. For example, in use, one or more therapeutic signals from the one or more generators may be provided to one or more electrodes, through the anatomy of the patient, and hack to the one or more generators via the one or more patient pads. In use, the one or more patient pads may be placed in at a remote location. For example, the one or more patient pads may be placed in physical contact, electrical contact, or both with a patient. In other words, depending on the type of medical procedure, the one or more patient pads may be in contact with a patient lying or sitting on the one or more patient pads; in contact with a patient's back; on or around an arm or leg of a patient; in contact with a patient chest; etc.

FIG. 1a illustrates a schematic circuit of an electrosurgical medical device 100. The electrosurgical medical device 100 includes a generator 102 and a hand piece 104. The generator 102 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114. A remote or patient pad 120 is in electrical communication with the electrosurgical medical device 100 and the therapy power supply 110.

A first therapeutic power connection 122, which includes a first therapeutic power switch 124, extends between the therapy power supply 110 and the first electrode 112. A second therapeutic power connection 126, which includes a second therapeutic power switch 128, extends between the therapy power supply 110 and the first electrode 112. A third therapeutic power connection 130 extends between the therapy power supply 110 and plug 133. From the plug 133, a common conductor wire 135 extends to the first electrode 112. Therapeutic power is transmitted from the therapy power supply 110 to the plug 133 via wire 130, and then from the plug 133 to the first electrode 112 via the common conductor wire 135. When the first therapeutic power switch 124, the second therapeutic power switch 128, or both is open, therapeutic power is restricted from communicating to the first electrode 112. However, when at least one of the first and second therapeutic power switches 124, 128 are closed, therapeutic power is provided from the therapy power supply 110 to the first electrode 112.

A first heating power connection 132 extends between the heating power supply 108 and the plug 133. From the plug 133, the common conductor wire 135 extends to the heater 114 of the first electrode 112. Heating power is transmitted from the heating power supply 108 to the plug 133 via wire 132, and then from the plug 133 to the heater 114 via the common conductor wire 135. The common conductor wire 135 is therefore adapted to carry two signals—a therapeutic power signal from the therapy power supply 110 to the first electrode 112 and a heating power signal from the heating power supply 108 to the heater 114. The two signals can be carried at the same time, or at different times for example one signal after the other. The plug 133 has two pins, and each of the pins connect to the individual power supplies 108, 110 the corresponding conductor wires or power connections 132, 130. The common conductor wire 135 connects to the plug 133 via a plug-and-socket connection. Alternatively, the common conductor wire 135 can be hard wired (e.g., permanently connected) to the plug 133.

A second heating power connection 134, which includes a heating power switch 136, extends between the heating power supply 108 and the first electrode 112. When the heating power switch 136 closed, heating power provided from the heating power source 108 to the heater 114 to heat the first electrode 112. When the heating power switch 136 is open, heating power is restricted from communicating to the heater 114 and, as such, the first electrode 112 is not heated.

A fourth therapeutic power connection 138 and a fifth therapeutic power connection 140 extends between the therapy power supply 110 and a corresponding second and third electrode 116, 118. A sixth therapeutic power connection 141, which includes an electrode switch 142, extends between the therapy power supply 110 and third electrode 118. A patient pad connection 144 extends between the therapy power supply 110 and the remote or patient pad 120.

When at least one of the first and second therapeutic power switches 124, 128 are closed, therapeutic power can be communicated from the therapy power supply 110 to the first electrode 112 and communicated back to the therapy power supply 110 via the second electrode 116, the third electrode 118, or both (i.e., bipolar mode). Alternatively, the therapeutic power can be communicated back to the therapy power supply 110 via the patient pad 120 (monopolar mode).

Moreover, by closing the electrode switch 142, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the heating power switch 136 can be opened to prevent the supply of heating power to the heater 114 while therapeutic power is being communicated between the second and third electrodes 116, 118. Moreover, one of the therapeutic power switches 124, 128 can be opened to prevent the supply of therapeutic power to the first electrode 112 while therapeutic power is being communicated between the second and third electrodes 116, 118.

Figure 1B:
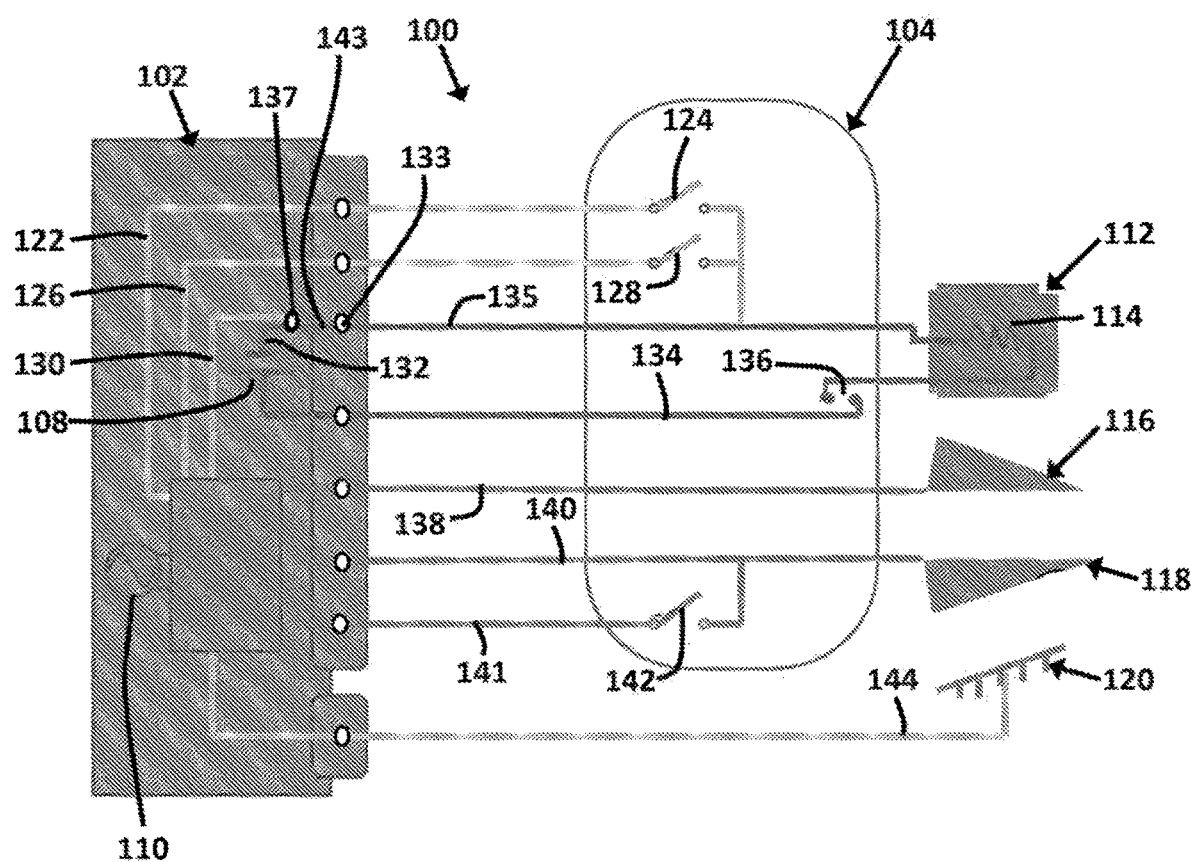
FIG. 1b is a schematic circuit of a medical device.

FIG. 1b illustrates a schematic circuit of an electrosurgical medical device 100. The electrosurgical medical device 100 includes a generator 102 and a hand piece 104. The generator 102 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114. A remote or patient pad 120 is in electrical communication with the electrosurgical medical device 100 and the therapy power supply 110.

A first therapeutic power connection 122, which includes a first therapeutic power switch 124, extends between the therapy power supply 110 and the first electrode 112. A second therapeutic power connection 126, which includes a second therapeutic power switch 128, extends between the therapy power supply 110 and the first electrode 112.

A third therapeutic power connection 130 extends between the therapy power supply 110 and a node 137. From the node 137, a common conductor wire 143 extends to a plug 133. A common conductor wire 135 is adapted to be connected to the plug 133 via a plug-and-socket connection. Alternatively, the conductor wire 135 can be hard wired to the plug 133. From the plug 133, the common conductor wire 135 extends to the first electrode 112. Therapeutic power is transferred from the therapy power supply 110 to the node 137 viii conductor wire 130, and from the node 137 to the plug 133 via conductor wire 143, and from the plug 133 to the first electrode 112 via the common conductor wire 135.

When the first therapeutic power switch 124, the second therapeutic power switch 128, or both is open, therapeutic power is restricted from communicating to the first electrode 112. However, when at least one of the first and second therapeutic power switches 124, 128 are closed, therapeutic power provided from the therapy power supply 110 to the first electrode 112.

A first heating power connection 132 extends between the heating power supply 108 and the node 137. From the node 137, the common conductor wire 143 extends to a plug 133. From the plug 133, the common conductor wire 135 extends to the heater 114. Heating power from the heating power supply 108 is provided to the node 137 via conductor wire 132, from the node 137 to the plug 133 via conductor wire 143, and from the plug 133 to the heater 114 via the common conductor wire 135. The common conductor wires 143, 135 therefore carry two signals—a therapeutic power signal from the therapy power supply to the heater 114 and a heating power signal from the heating power supply 108 to the heater 114. The two signals can be carried at the same time, or at different times for example one signal after the other. The plug 133 has a single pin, and the single pin connects from the plug 133 to the common conductor wire 143 which then connects to the individual wires power supplies 108, 110 via the corresponding conductor wires or connections 132, 130 at node 137.

A second heating power connection 134, which includes a heating power switch 136, extends between the heating power supply 108 and the first electrode 112. When the heating power switch 136 is closed, heating power provided from the heating power source 108 to the heater 114 to heat the first electrode 112. When the heating power switch 136 is open, heating power is restricted from communicating to the heater 114 and, as such, the first electrode 112 is not heated.

A fourth therapeutic power connection 138 and a fifth therapeutic power connection 140 extends between the therapy power supply 110 and a corresponding second and third electrode 116, 118. A sixth therapeutic power connection 141, which includes an electrode switch 142, extends between the therapy power supply 110 and third electrode 118. A patient pad connection 144 extends between the therapy power supply 110 and the remote or patient pad 120.

When at least one of the first and second therapeutic power switches 124, 128 are closed, therapeutic power can be communicated from the therapy power supply 110 to the first electrode 112 and communicated back to the therapy power supply 110 via the second electrode 116, the third electrode 118, or both (i.e., bipolar mode). Alternatively, the therapeutic power can be communicated back to the therapy power supply 110 via the patient pad 120 (monopolar mode).

Moreover, by closing the electrode switch 142, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the heating power switch 136 can be opened to prevent the supply of heating power to the heater 114 while therapeutic power is being communicated between the second and third electrodes 116, 118. Moreover, one of the therapeutic power switches 124, 128 can be opened to prevent the supply of therapeutic power to the first electrode 112 while therapeutic power is being communicated between the second and third electrodes 116, 118.

Figure 1C:
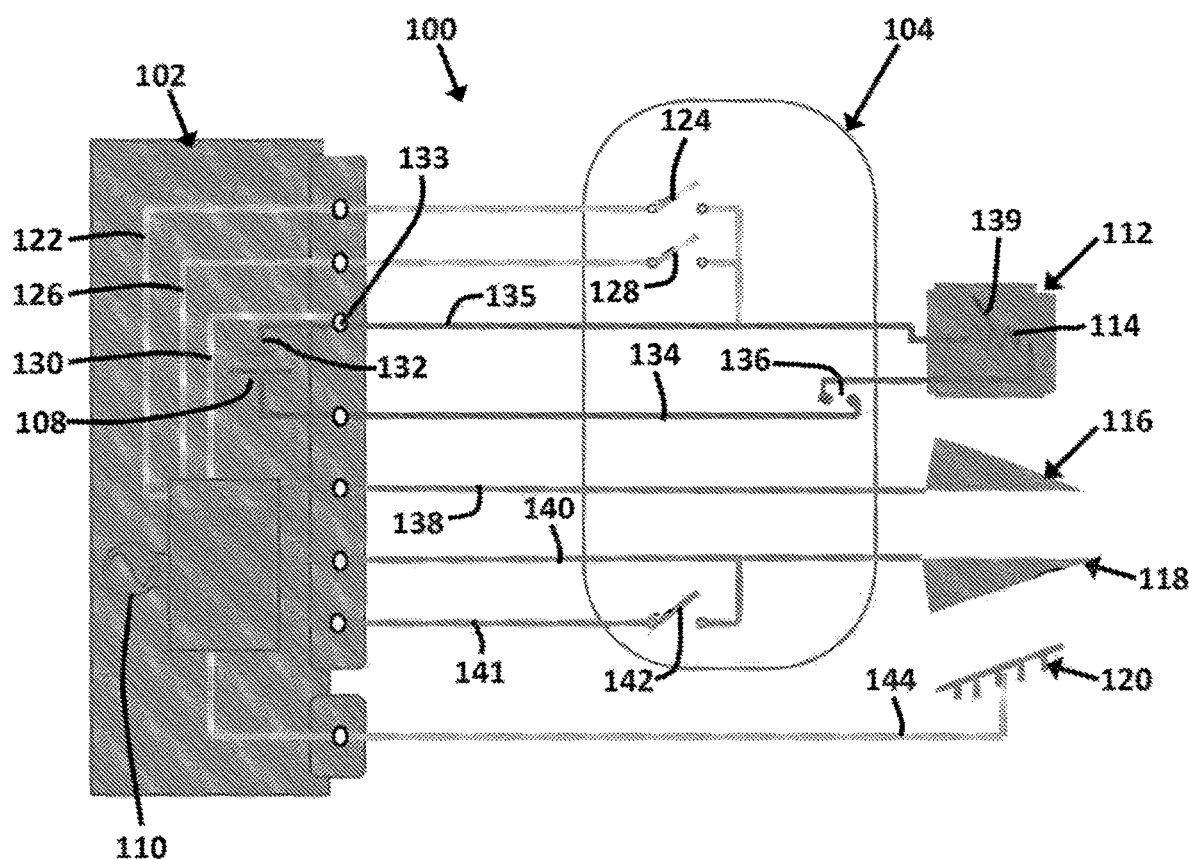
FIG. 1c is a schematic circuit of a medical device.

FIG. 1c illustrates a schematic circuit of an electrosurgical medical device 100. The electrosurgical medical device 100 includes a generator 102 and a hand piece 104. The generator 102 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114. A remote or patient pad 120 is in electrical communication with the electrosurgical medical device 100 and the therapy power supply 110.

A first therapeutic power connection 122, which includes a first therapeutic power switch 124, extends between the therapy power supply 110 and the first electrode 112. A second therapeutic power connection 126, which includes a second therapeutic power switch 128, extends between the therapy power supply 110 and the heater 144. From the heater 114, a conductor wire 139 is connected to the first electrode 112.

A third therapeutic power connection 130 extends between the therapy power supply 110 and plug 133. From the plug 133, a common conductor wire 135 extends to the first electrode 112. Therapeutic power or a signal is provided from the therapy power supply 110 to the plug 133 via conductor wire 130, from the plug 133 to the heater 114 via conductor wire 135, and from the heater 114 to the first electrode 112 via the conductor wire 139. When the first therapeutic power switch 124, the second therapeutic power switch 128, or both is open, therapeutic power is restricted from communicating to the heater 114 and then to the first electrode 112. However, when at least one of the first and second therapeutic power switches 124, 128 are closed, therapeutic power is provided from the therapy power supply 110 to the heater and then to the first electrode 112 via wire 139.

A first heating power connection 132 extends between the heating power supply 108 and the plug 133. The heating power is provided from the heating power supply 108 to the plug 133 via conductor wire 132, and from the plug 133 to the heater 114 via common conductor wire 135. The common conductor wire 135 carries two signals—therapeutic power from the therapy power supply 110 to the heater 114 and heating power from the heating power supply 108 to the heater 114. The plug 133 has two pins, and each of the pits connect the common conductor wire 135 to the individual power supplies 108, 110 via the corresponding conductor wires or connections 132, 130. Alternatively, the plug 133 can have a single pin, which connects to a node, as was illustrated and described in FIG. 1*b*.

A second heating power connection 134, which includes a heating power switch 136, extends between the heating power supply 108 and the first electrode 112. When the heating power switch 136 is closed, heating power is provided from the heating power source 108 to the heater 114 to heat the first electrode 112. When the heating power switch 136 is open, heating power is restricted from communicating to the heater 114 and, as such, the first electrode 112 is not heated.

A fourth therapeutic power connection 138 and a fifth therapeutic power connection 140 extends between the therapy power supply 110 and a corresponding second and third electrode 116, 118. A sixth therapeutic power connection 141, which includes an electrode switch 142, extends between the therapy power supply 110 and third electrode 118. A patient pad connection 144 extends between the therapy power supply 110 and the remote or patient pad 120.

When at least one of the first and second therapeutic power switches 124, 128 are closed, therapeutic power can be communicated from the therapy power supply 110 to the first electrode 112 and communicated back to the therapy power supply 110 via the second electrode 116, the third electrode 118, or both (i.e., bipolar mode). Alternatively, the therapeutic power can be communicated back to the therapy power supply 110 via the patient pad 120 (monopolar mode).

Moreover, by closing the electrode switch 142, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the heating power switch 136 can be opened to prevent the supply of heating power to the heater 114 while therapeutic power is being communicated between the second and third electrodes 116, 118. Moreover, one of the therapeutic power switches 124, 128 can be opened to prevent the supply of therapeutic power to the first electrode 112 while therapeutic power is being communicated between the second and third electrodes 116, 118.

Figure 1D:
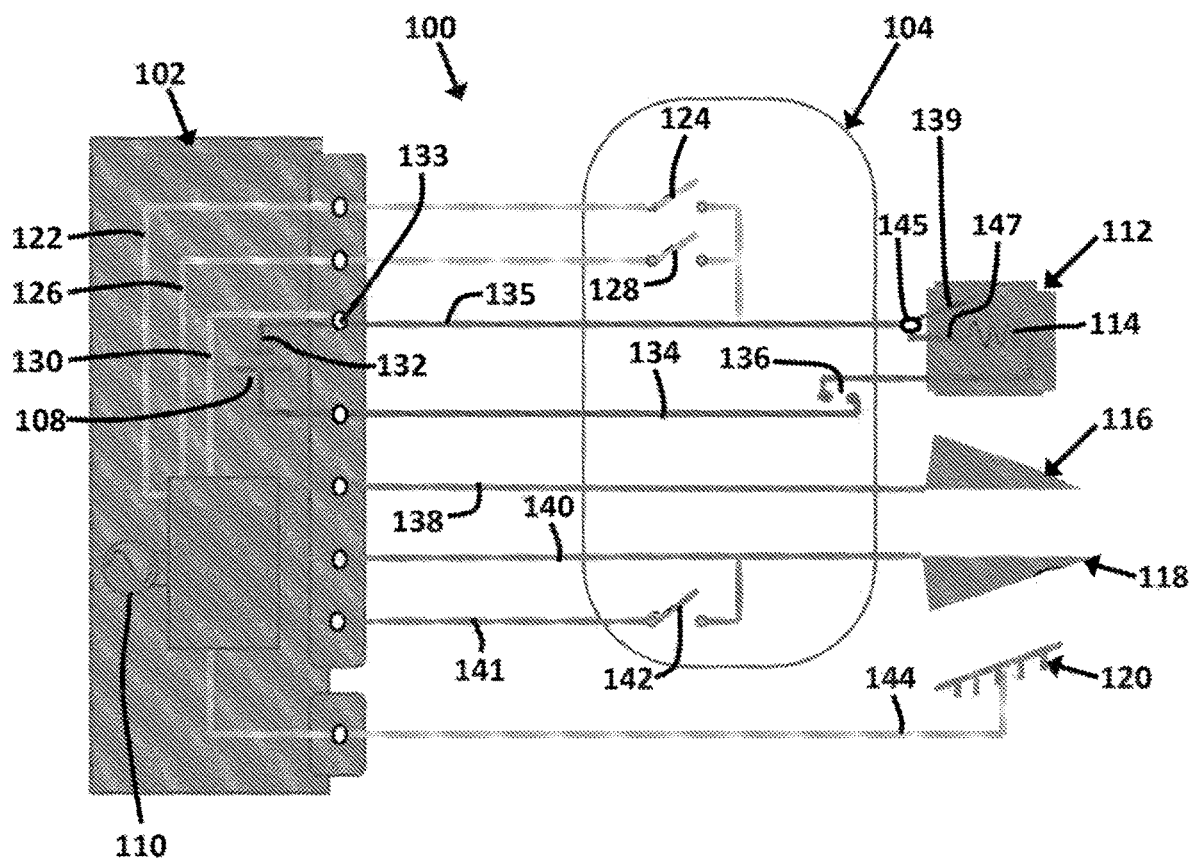
FIG. 1d is a schematic circuit of a medical device.

FIG. 1*d* illustrates a schematic circuit of an electrosurgical medical device 100. The electrosurgical medical device 100 includes a generator 102 and a hand piece 104. The generator 102 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114. A remote or patient pad 120 is in electrical communication with the electrosurgical medical device 100 and the therapy power supply 110.

A first therapeutic power connection 122, which includes a first therapeutic power switch 124, extends between the therapy power supply 110 and the first electrode 112. A second therapeutic power connection 126, which includes a second therapeutic power switch 128, extends between the therapy power supply 110 and the first electrode 112. A third therapeutic power connection 130 extends between the therapy power supply 110 and plug 133. From the plug 133, a common conductor wire 135 extends to a node or connection 145. The common conductor wire 135 connects to the plug 133 via a plug-and-socket connection. Alternatively, the common conductor wire 135 can be hard-wired or permanently connected to the plug 133. From the node or connection 145, a conductor wire 139 extends to the first electrode 112. The therapeutic power is provided from the therapy power supply 110 to the plug 133 via conductor wire 130, from the plug 133 to the node 145 via common conductor wire 135, and from the node 145 to the first electrode 112 via conductor wire 139. When the first therapeutic power switch 124, the second therapeutic power switch 128, or both is open, therapeutic power is restricted from communicating to the first electrode 112. However, when at least one of the first and second therapeutic power switches 124, 128 are closed, therapeutic power is provided from the therapy power supply 110 to the first electrode 112.

A first heating power connection 132 extends between the heating power supply 108 and the plug 133. Heating power is provided from the heating power supply 108 to the plug 133 via conductor wire 132, from the plum 133 to the node 145 via common conductor wire 135, and from the node 145 to the heater 114 via conductor wire 147. The common conductor wire 135 carries two signals—a therapeutic power signal from the therapy power supply to the node 145 and then ultimately to the first electrode 112 via wire 139, and a heating power signal from the heating power supply 108 to the node 145 and then ultimately to the heater 114 via wire 147. The two signals can be carried at the same time, or at different times for example one signal after the other. The plug 133 has two pins, and each of the pins connect to the individual power supplies 108, 110 via the corresponding conductor wires or connections 132, 130. Alternatively, the plug 133 can have a single pin, which connects to a node, as was illustrated and described in FIG. 1*b*.

A second heating power connection 134, which includes a heating power switch 136, extends between the heating power supply 108 and the first electrode 112. When the heating power switch 136 is closed, heating power is provided from the heating power source 108 to the heater 114 to heat the first electrode 112. When the heating power switch 136 is open, heating power is restricted from communicating to the heater 114 and, as such, the first electrode 112 not heated.

A fourth therapeutic power connection 138 and a fifth therapeutic power connection 140 extends between the therapy power supply 110 and a corresponding second and third electrode 116, 118. A sixth therapeutic power connection 141, which includes an electrode switch 142, extends between the therapy power supply 110 and third electrode 118. A patient pad connection 144 extends between the therapy power supply 110 and the remote or patient pad 120.

When at least one of the first and second therapeutic power switches 124, 128 are closed, therapeutic power can be communicated from the therapy power supply 110 to the first electrode 112 and communicated back to the therapy power supply 110 via the second electrode 116, the third electrode 118, or both (i.e., bipolar mode). Alternatively, the therapeutic power can be communicated back to the therapy power supply 110 via the patient pad 120 (monopolar mode).

Moreover, by closing the electrode switch 142, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the heating power switch 136 can be opened to prevent the supply of heating power to the heater 114 while therapeutic power is being communicated between the second and third electrodes 116, 118. Moreover, one of the therapeutic power switches 124, 128 can be opened to prevent the supply of therapeutic power to the first electrode 112 while therapeutic power is being communicated between the second and third electrodes 116, 118.

Figure 2A:
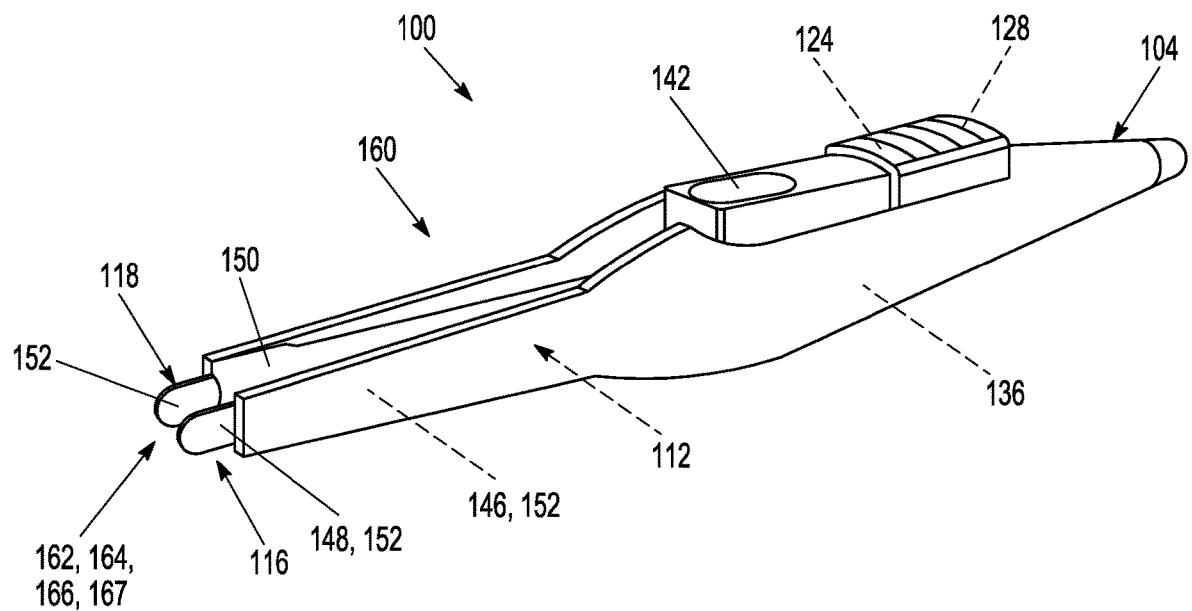
FIG. 2a is a perspective view of a medical device.

FIG. 2a illustrates an exemplary electrosurgical medical device 100 in a bipolar operating mode 160. The electrosurgical medical device 100 includes a hand piece 104, a first extension 146, a second extension 148, and a third extension 150. The extensions 146, 148, 160 include at least one function feature 152. The first electrode 112 is in communication with the first extension 146, the second electrode 116 is in communication with the second extension 148, and the third electrode 118 is in communication with the third extension 150. The first extension 146 is longitudinally moveable relative to both the second and third extensions 148, 150. That is, the first extension 146 can be independently moved and extended beyond the second extension 148 and the third extension 150, and can be retracted therebetween. To perform a device function in the bipolar operating mode 160, the electrosurgical medical device 100, and more specifically, the electrodes and the extensions can be used in a variety of arrangements, such as a first arrangement 162, a second arrangement 164, a third arrangement 166, and a fourth arrangement 167.

With reference to FIGS. 1 and 2a, in the first arrangement 162, therapeutic power is provided to the second and third electrodes 116, 118. More specifically, therapeutic power is provided from the therapy power supply 110 to the second electrode 116 via the fourth therapeutic power connection 138. The electrode switch 142 is closed and therapeutic power is provided from the therapy power supply 110 to the third electrode 118. Accordingly, therapeutic power can flow between the second and third electrodes 116, 118. In use, a selected portion of the anatomy can be placed between the second and third extensions 148, 150 and in contact with the functional features 152 of one or both of the extensions 148, 150. Thus, a device function can be performed on that portion of the anatomy using the second and third electrodes 116, 118.

In the second arrangement 164, therapeutic power is provided to the first and second electrodes 112, 116. More specifically, therapeutic power is provided from the therapy power supply 110 to the first electrode 112 via the third therapeutic power connection 130, and to the second electrode 116 via the fourth therapeutic power connection 138. Accordingly, therapeutic power flows between the first and second electrodes 112, 116. In use, a selected portion of the anatomy can be placed between the first and second extensions 146, 148, and in contact with at least one of the functional features 152 thereof. Thus, a device function can be performed using the first and second electrodes 112, 116. While performing a device function in the second bipolar configuration 164, the first electrode 112 can be optionally heated. That is, by closing the heating power switch 136 and supplying heating power from the heating power supply 108 to the heater 114, the first electrode 112 can be resistively heated. Moreover, by closing one or both of the switches 124, 128, therapeutic power can be provided from the therapy power supply 110 to the first electrode 112 and back to the therapy power supply 110 via the remote or patient pad 120 (not illustrated).

Figure 4:
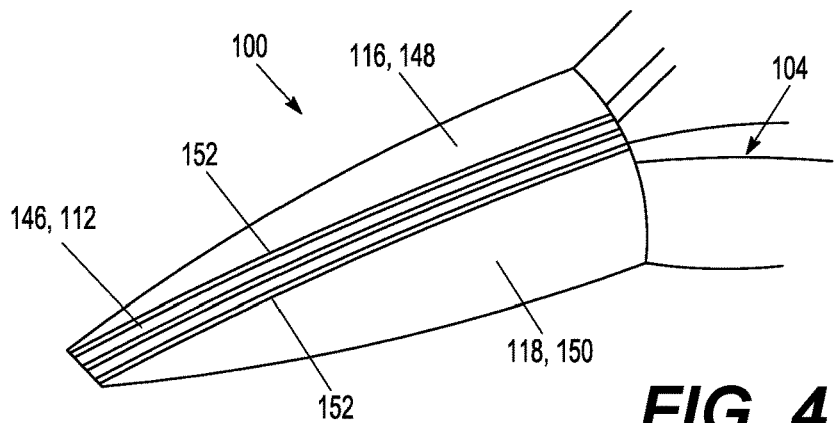
FIG. 4 is a perspective view of a medical device.
Figure 5:
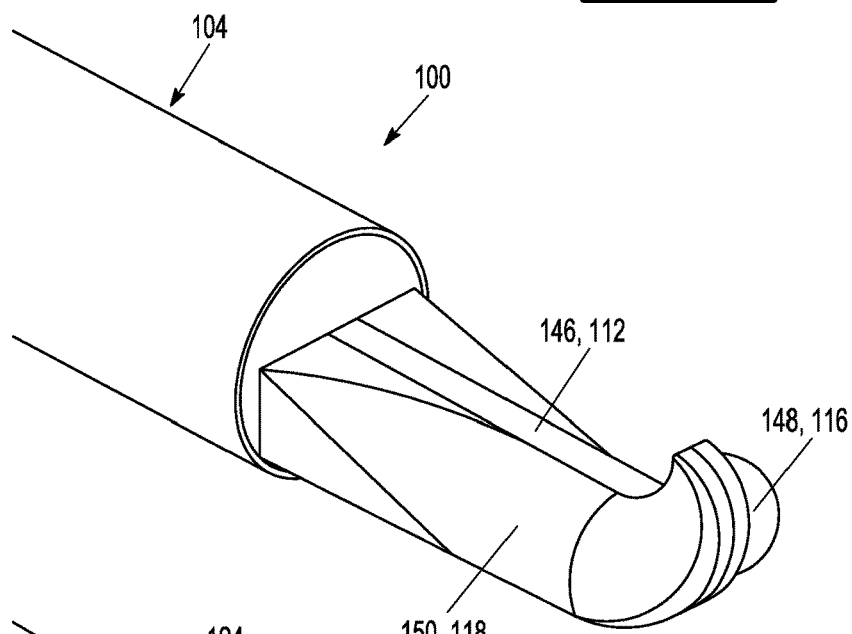
FIG. 5 is a perspective view of a medical device.
Figure 6:
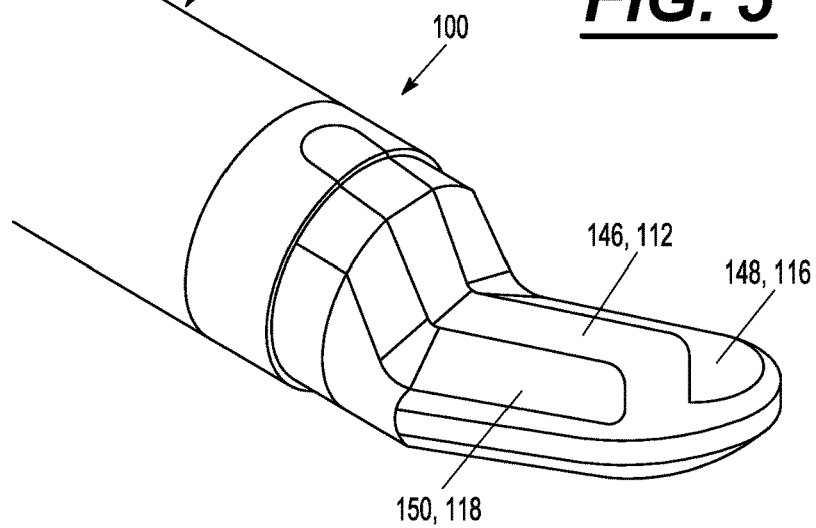
FIG. 6 is a perspective view of a medical device.

In the third arrangement 166, which may be also relevant to the electrosurgical medical devices 100 shown in FIGS. 4-6, therapeutic power is provided to the first and third electrodes 112, 118. More specifically, therapeutic power is provided from the therapy power supply 110 to the first electrode 112 via the third therapeutic power connection 130. The electrode switch 142 is closed and therapeutic power is provided from the therapy power supply 110 to the third electrode 118. Accordingly, therapeutic power flows between the first and third electrodes 112, 118. In use, a selected portion of the anatomy can be placed between the first and third extensions 146, 150, and in contact with at least one of the functional features 152 thereof. Thus, a device function can be performed using the first and third electrodes 112, 118. While performing a device function in this arrangement, the first electrode 112 can be optionally heated. That is, by closing the heating power switch 136 and supplying heating power from the heating power supply 108 to the heater 114, the first electrode 112 can be resistively heated. Moreover, by closing one or both of the switches 124, 128, therapeutic power can be provided from the therapy power supply 110 to the first electrode 112 and back to the therapy power supply 110 via the remote or patient pad 120 (not illustrated).

In the fourth arrangement 167, therapeutic power is communicated between to the first electrode and both the second and third electrodes 116, 118. More specifically, therapeutic power is provided from the therapy power supply 110 to the first electrode 112 via the third therapeutic power connection 130. The electrode switch 142 is closed and at least a portion of the therapeutic power can be provided from the first electrode 112 to the third electrode 118 and back to the therapy power supply 110. Additionally, at least another portion of the therapeutic power can be provided from the first electrode 112 to the second electrode 116 and back to the therapy power supply 110. While performing a device function in the fourth bipolar configuration 167, the first electrode 112 can be optionally heated. That is, by closing the heating power switch 136 and supplying heating power from the heating power supply 108 to the heater 114, the first electrode 112 can be resistively heated.

Figure 2B:
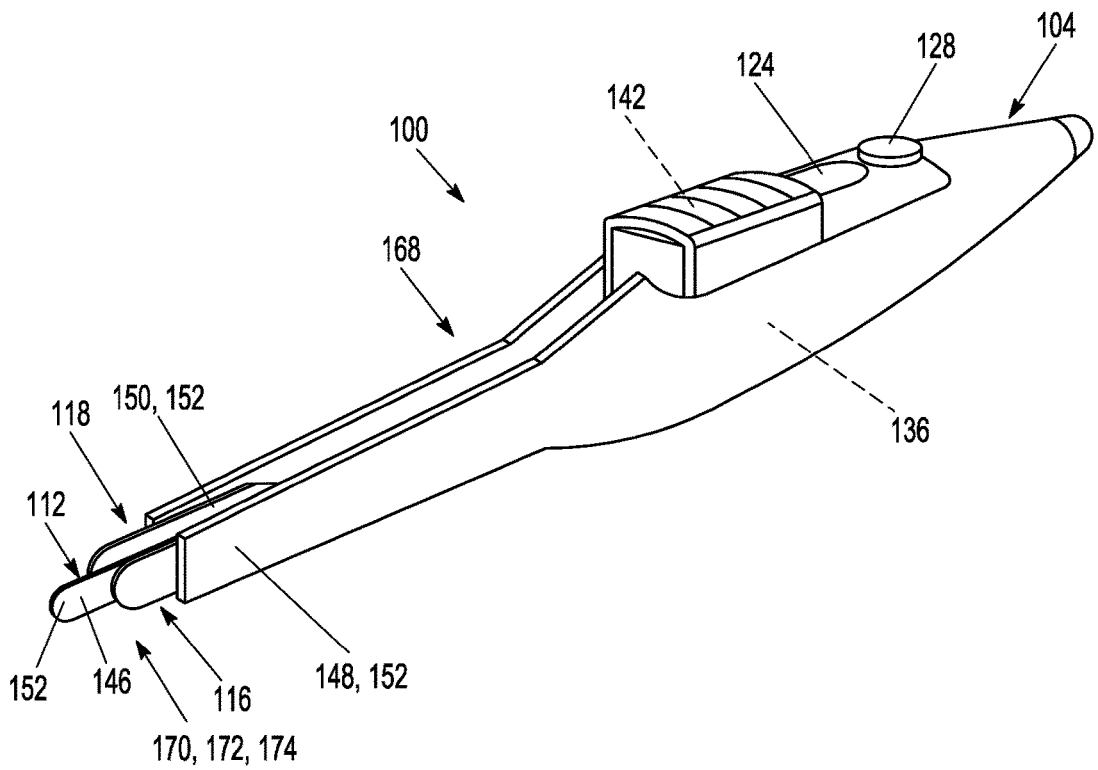
FIG. 2b is a perspective view of a medical device.

FIG. 2b illustrates an electrosurgical medical device 100 in a monopolar operating mode 168. In the monopolar operating mode 168, the electrosurgical medical device 100 can be used in a fifth arrangement 170, a sixth arrangement 172, and a seventh arrangement 174.

With refinance to FIGS. 1 and 2b, in the fifth arrangement 170, therapeutic power is provided to the first electrode 112. More specifically, therapeutic power is provided from the therapy power supply 110 to the first electrode 112 via first electrode therapy power supply connection 130. By closing one or both of the switches 124, 128, therapeutic power can be provided to the first electrode 112 via the first therapeutic power connection 122 and/or second therapeutic power connection 126 respectively. During use, the therapeutic power can communicate from the therapy power supply 108 to the first electrode 112, through the anatomy, to the patient pad 120 and back to the therapy power supply 110 via the patient pad connection 144. In use, the functional feature 152 of the first extension 146 can contact a selected portion of the anatomy, and a device function can be performed on that portion of the anatomy. The first electrode 112 can also be optionally and/or selectively heated. That is, by supplying heating power from the heating power supply 108 to the heater 114, the first electrode 112 can be resistively heated.

In the sixth arrangement 172, therapeutic power is provided from the therapeutic power supply 110 to the second electrode 116 via the second electrode therapeutic power supply connection 138. The therapeutic power can communicate through the patient pad 120 to the therapeutic power supply 110 via the patient pad connection 144. Accordingly, therapeutic power flows between the second electrode 116 and the patient pad 120. In use, the functional feature 152 the second extension 148 can contact a selected portion of the anatomy, and a device function can be performed using the second electrode 116. The first electrode 112 can be optionally heated by supplying heating power from the heating power supply 108 to the heater 114.

In the seventh arrangement 174, the electrode switch 142 is closed so that therapeutic power is provided from the therapeutic power supply 110 to the third electrode 118. The therapeutic power can communicate through the patient pad 120 to the therapeutic power supply 110 via the patient pad connection 144. Accordingly, therapeutic power flows between the third electrode 118 and the patient pad 120. In use, the functional feature 152 of the third extension 150 can contact a selected portion of the anatomy, and a device function can be performed using the third electrode 118. The first electrode 112 can be optionally heated by supplying heating power from the heating power supply 108 to the heater 114.

Figure 3:
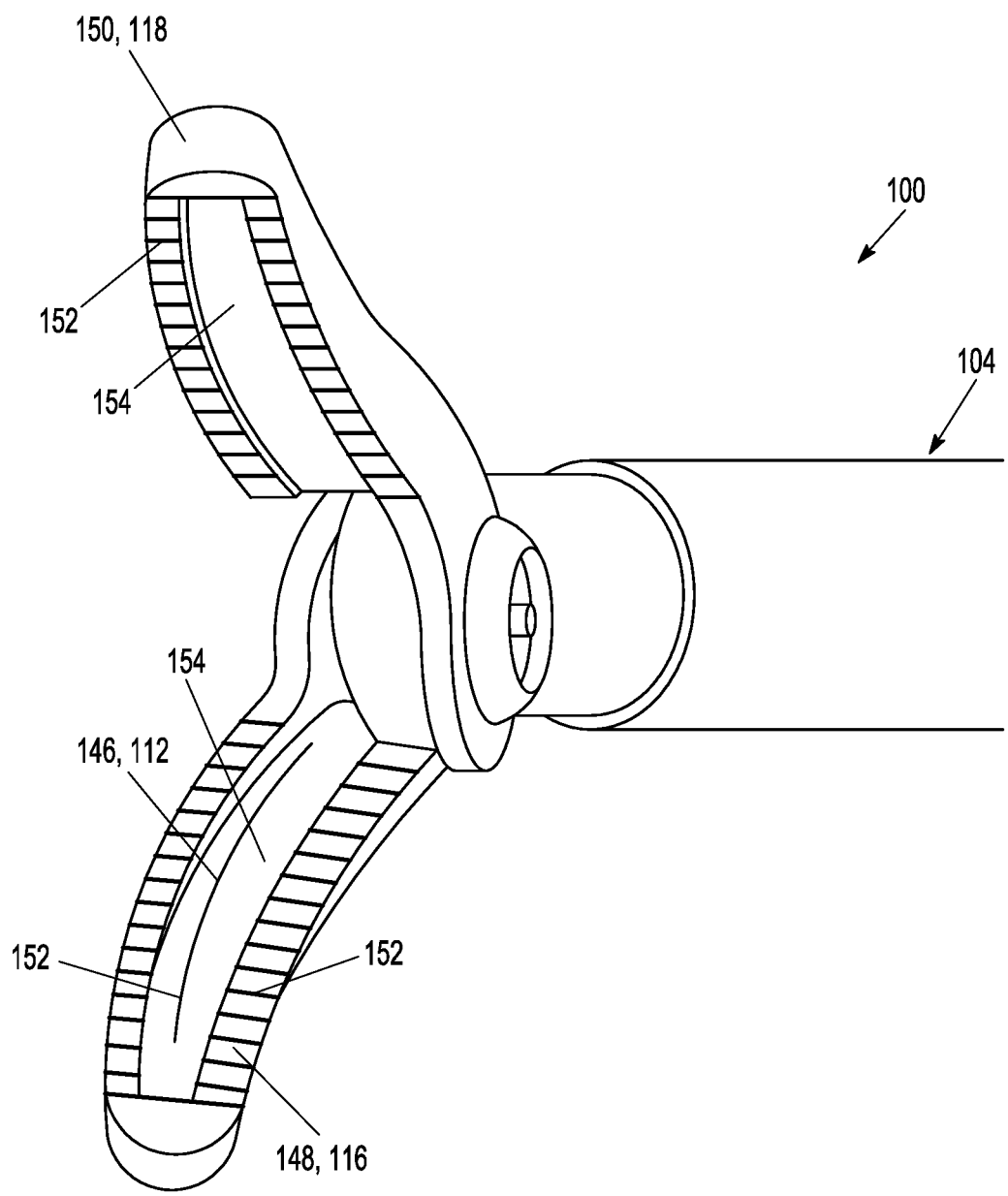
FIG. 3 is a perspective view of a medical device.

FIG. 3 illustrates an exemplary electrosurgical medical device 100. The electrosurgical medical device 100 includes a hand piece 104, a first electrode 112 in communication with a first extension 146, a second electrode 116 in communication with a second extension 148, and a third electrode 118 in communication with a third extension 150. Optionally, the first electrode 112 can be in communication with the second extension 148. Optionally, the second extension 148 and the third extension 150 can be the same or connected. The second and third extensions 116, 118 include an insulating material 154 intended to restrict or prevent accidental arcing and/or heat transfer between the electrodes. Each of the extensions 146, 148, 150 includes a functional feature 152. More specifically, the function features 152 on the second and third extensions 148, 150 can be teeth, while the functional feature 152 associated with the first extension 146 can be a blade. The electrosurgical medical device 100 of FIG. 3 may be substantially similar to the medical devices shown in FIGS. 2a and 2b, except that the first extension 146 is generally stationary (e.g., is not independently moveable) relative to the second extension 148. However, the electrosurgical medical device 100 of FIG. 3 can perform in one or more of the aforementioned modes. That is, the electrodes and the extensions can be used in one or more of the arrangements described in FIGS. 2a and 2b. For example, therapeutic power can be communicated to the first electrode 112, to or through tissue, and back to the therapy power supply 110 via the patient pad 120 (not illustrated), via one or both of the second and third electrode 116, 118, or a combination thereof. Likewise, the first electrode 112 can be optionally heated. That is, by supplying heating power from the heating power supply 108 to the heater 114, the first electrode 112 can be resistively heated. In other arrangements, therapeutic power can be supplied between the second and third electrodes 116, 118 and back to the therapy power supply 110.

FIG. 4 illustrates an exemplary electrosurgical medical device 100. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes may be in communication with one or more extensions. Optionally, two or more extensions may be the same or connected together. At least one of the extensions 146, 148, 150 includes a functional feature 152 (not illustrated). The electrosurgical medical device 100 of FIG. 4 may be substantially similar to one or more of the medical devices 100 of FIGS. 2a-3 and 5-6. In other words, the electrosurgical medical device 100 of FIG. 4 can function and perform in one or more of the aforementioned modes and configurations. For example, in one configuration, therapeutic power can be communicated to the first electrode 112, to or through tissue, and back to the therapy power supply 110 via the patient pad 120 (not illustrated), via the second electrode 116, the third electrode 118, or a combination thereof. Likewise, the first electrode 112 can be optionally heated. That is, by supplying heating power from the heating power supply 108 to the heater 114, the first electrode 112 can be restively heated. In other configurations, therapeutic power can be supplied between the second and third electrodes 116, 118 and back to the therapy power supply 110. Moreover, the first extension 146 may or may not move in relation to the second and third extensions 148, 150, which may also move or be restricted from moving. The extensions 116, 118 of FIG. 4 also include an in material 152 intended to restrict or prevent arcing and/or heat transfer between the electrodes 112, 116, 118.

FIG. 5 illustrates an exemplary electrosurgical medical device 100, which may be a J Hook. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes may be in communication with one or more extensions. Optionally, two or more extensions may be the same or connected together. At least one of the extensions 146, 148, 150 includes a functional feature 152 (not illustrated). The electrosurgical medical device 100 of FIG. 5 may be substantially similar to one or more of the medical device shown and described in FIGS. 2a, 2b and 3-6. In other words, the electrosurgical medical device 100 of FIG. 4 can function and perform in one or more of the aforementioned modes and configurations. For example, therapeutic power can be communicated to the first electrode 112, to or through tissue, and back to the therapy power supply 110 via the patient pad 120 (not illustrated), one or both of the second and third electrodes 116, 118, or a combination thereof. Likewise, the first electrode 112 can be optionally heated. That is, by supplying heating power from the heating power supply 108 to the heater 114, the first electrode 112 can be resistively heated. In other configurations, therapeutic power can be supplied between the second and third electrodes 116, 118 and back to the therapy power supply 110. Moreover, the first extension may or may not move relative to the second and third extensions 148, 150.

FIG. 6 illustrates an exemplary electrosurgical medical device 100, which may be a medical spatula. The electrosurgical medical device 100 includes a hand piece 104, a first electrode 112 in communication with a first extension 146, a second electrode 116 in communication with a second extension 148, and a third electrode 118 in communication with a third extension 150. Optionally, two or more electrodes tray be in communication with one or more extensions. Optionally, two or more extensions may be the same or connected together. At least one of the extensions 146, 148, 150 includes a functional feature 152 (not illustrated). The electrosurgical medical device 100 of FIG. 6 may be substantially similar to the medical device of FIGS. 2a, 2b, and 3. In other words, the electrosurgical medical device 100 of FIG. 4 can function and perform in one or more of the aforementioned modes and configurations. For example, therapeutic power can be communicated to the first electrode 112 to or through tissue and back to the therapy power supply 110 via the patient pad 120 (not illustrated), the second electrode 116, the third electrode 118, or a combination thereof. Likewise, the first electrode 112 can be optionally heated. That is, by supplying heating power from the heating. In other configurations, therapeutic power can be supplied between the second and third electrodes 116, 118 and back to the therapy power supply 110, power supply 108 to the heater 114, the list electrode 112 can be resistively heated. Moreover, the first extension may or may not move relative to the second and third extensions 148, 150.

Figure 7:
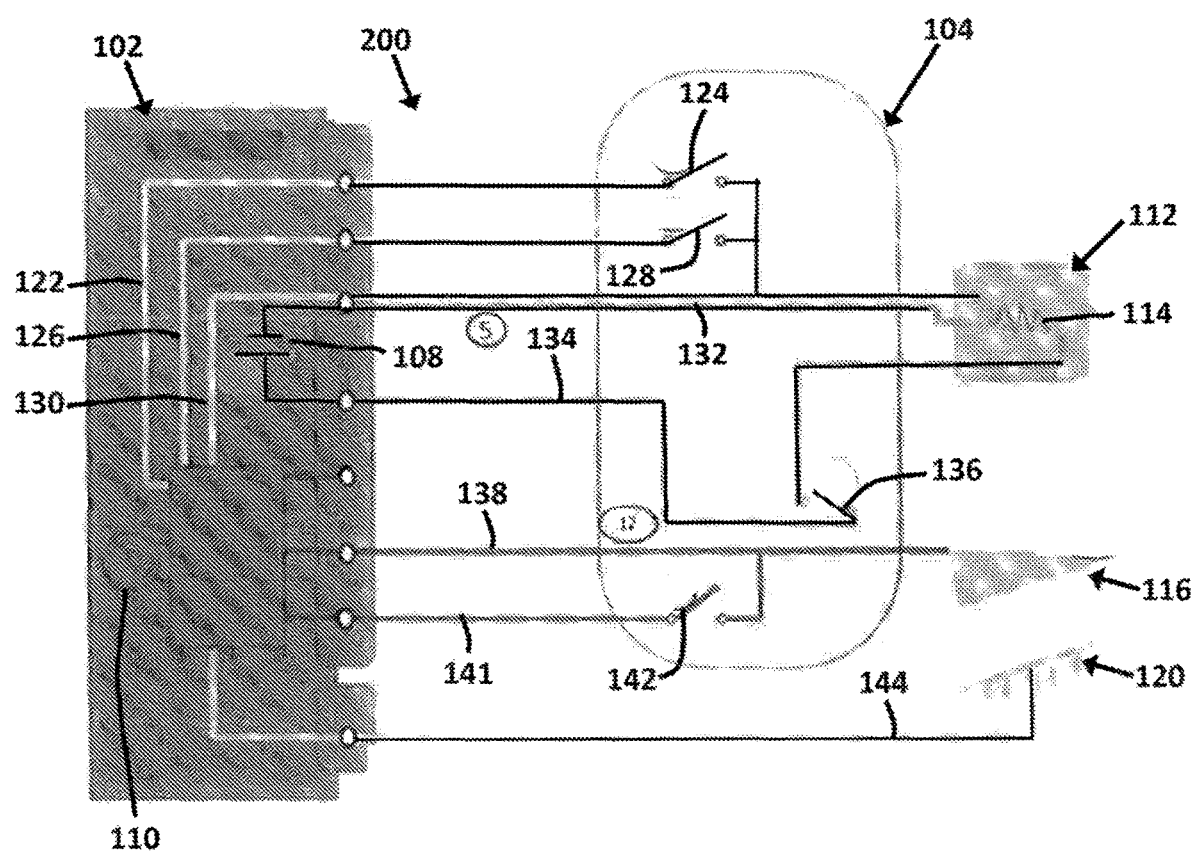
FIG. 7 is a schematic of a circuit of a medical device.

FIG. 7 illustrates a schematic circuit of an electrosurgical medical device 200. The medical device 200 generally includes an electrosurgical generator 102 and a hand piece 104. The electrosurgical generator 102 includes a heating power supply 108 and a therapy power supply 110. The heating power supply 108 provides heating power to the electrosurgical medical device 200, and the therapy power supply 110 provides therapeutic power to the electrosurgical medical device 200. The electrosurgical medical device 200 includes a first electrode 112, which may comprise a heater 114, and a second electrode 116. A patient pad 120 is in electrical communication with the electrosurgical medical device 200 and the therapy power supply 110.

A first therapeutic power connection 122, which includes a first therapeutic power switch 124, extends between the therapy power supply 110 and the first electrode 112. The first therapeutic power switch 124 provides selective communication of therapeutic power between the therapy power supply 110 and the first electrode 112. A second therapeutic power connection 126, which includes a second therapeutic power switch 128, extends between the therapy power supply 110 and the first electrode 112. The second monopolar therapeutic power switch 128 provides selective communication of therapeutic power between the therapy power supply 110 and the first electrode 112. A third therapeutic power connection 130 extends between the therapy power supply 110 and the first electrode 112, which provides therapeutic power to the first electrode 112. When one or both of the first and second therapeutic power switches 124, 128 are closed, therapeutic power is provided to the first electrode 112.

A first heating power connection 132 extends between the heating power supply 108 and the heater 114 of the first electrode 112. A second heating power connection 134, which includes a heating power switch 136, extends between the heating power supply 108 and the first electrode 112. When the heating power switch 136 is closed, heating power provided to the heater 114 to heat the first electrode 112. When the heating power switch 136 is open, heating power is restricted from communicating to the heater 114 and, as such, the first electrode 112 is not heated.

A fourth therapeutic power connection 138 extends between the therapy power supply 110 and the second electrode 116. A sixth therapeutic power connection 141, which includes an electrode switch 142, extends between the therapy power supply 110 and third electrode 118. Closing the electrode switch 142 can provide therapeutic power from the therapy power supply 110 to the second electrode 116. A patient pad connection 144 extends between the therapy power supply 110 and the patient pad 120.

In a bipolar operating mode, at least one of the switches 124, 128 are closed and therapeutic power is communicated from the therapy power supply 110 to the first electrode 112 and back to the therapy power supply 110 via the second electrode 116, (i.e., bipolar mode). Alternatively, in a monopolar operating mode, the first electrode therapeutic power circuit can be closed by communicating the therapeutic power from the therapy power supply 110 to the first electrode 112 and back to the therapy power supply 110 via a remote or patient pad 120.

Figure 8A:
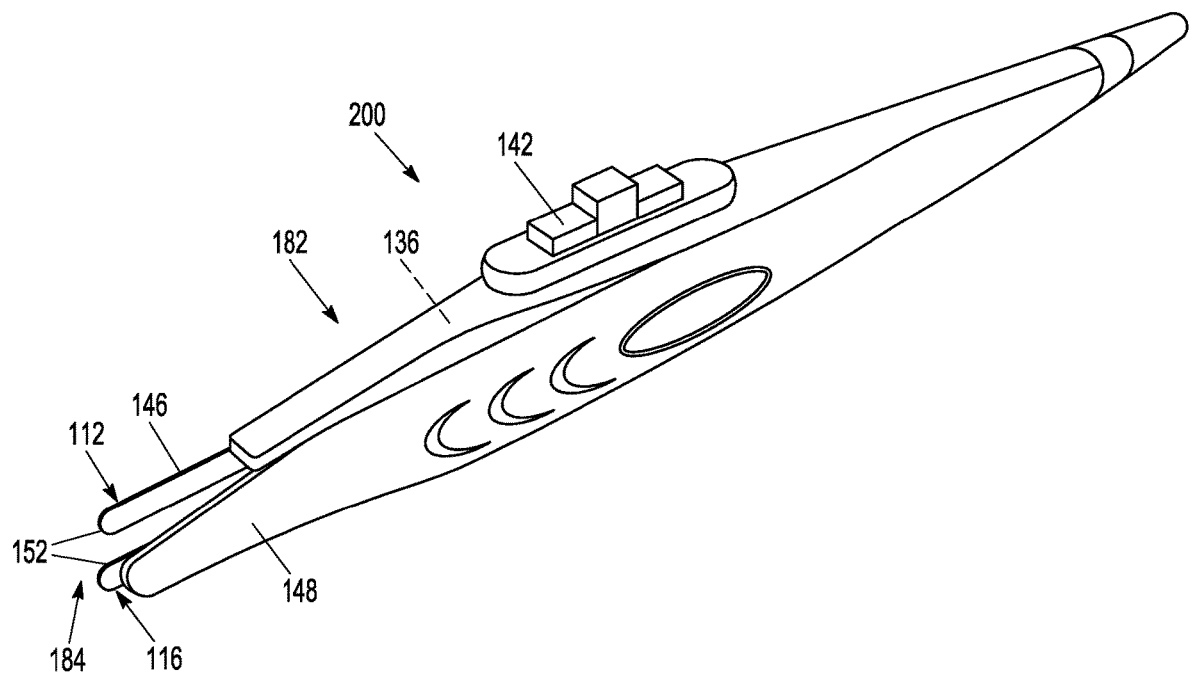
FIG. 8a is a perspective view of a medical device.

FIG. 8a illustrates an exemplary electrosurgical medical device 200 in a bipolar mode 182. The medical device 200 includes a hand piece 104 comprising a first extension 146 and a second extension 148. Each extension 146, 148 includes a functional feature 152. The first electrode 112 is in communication with the first extension 146, and the second electrode 116 is in communication with the second extension 148. The first extension 146 is moveable relative to the second extension 148. In the bipolar mode 182, the medical device 200 can perform a device function in an eighth configuration 184.

With reference to FIGS. 7 and 8a, in the eighth arrangement 184, therapeutic power is provided to the first and second electrodes 112, 116. More specifically, therapeutic power provided from the therapy power supply 110 to the first electrode 112 via the first electrode therapy power supply connection 130. The therapeutic power is provided to the second electrode 116 via the second electrode therapy power supply connection 138 and the fourth electrode therapy supply connection 141 (i.e., closing electrode switch 142). Accordingly, therapeutic power flows between the first and second electrodes 112, 116. In use, a selected portion of the anatomy can be placed between the functional features 152 of the first and second extensions 146, 148, and a device function can be performed on that portion of the anatomy. While performing a device function in the eighth configuration 184, the first electrode 112 can be optionally heated. That is, by closing the heating power switch 136 and supplying heating power from the heating power supply 108 to the heater 114, the first electrode 112 can be resistively heated.

Figure 8B:
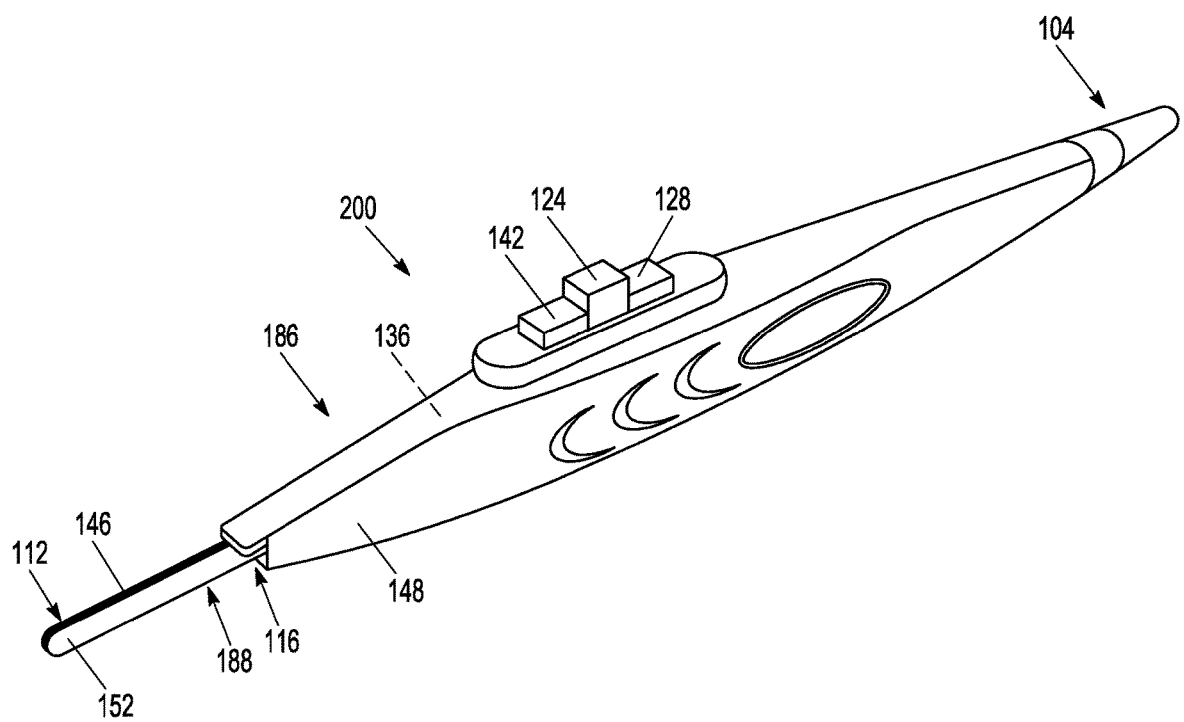
FIG. 8b is a perspective view of a medical device.

FIG. 8b illustrates the electrosurgical medical device 200 in a monopolar operating mode 186. In the monopolar operating mode 186, the medical device 200 can be used in a ninth configuration 188.

With reference to FIGS. 7 and 8b, in the ninth arrangement 188, therapeutic power is provided to the first electrode 112. That is, therapeutic power is provided from the therapy power supply 110 to the first electrode 112 via first electrode therapy power supply connection 130. By closing a respective switch 124, 128, therapeutic power can be provided from the therapy power supply 110 to the first electrode 112 via the first therapeutic power connection 122 and/or second therapeutic power connection 126. The therapeutic power can communicate through the patient pad 120 to the therapy power supply 110 via the patient pad connection 144. Accordingly, therapeutic power flows between the first electrode 112 and the patient pad 120. In use, the functional feature 152 of the first extension 146 can contact a selected portion of the anatomy, and a device function can be performed. The first electrode 112 can be optionally heated. That is, by supplying heating power from the heating power supply 108 to the heater 114, the first electrode 112 can be resistively heated.

It is understood that the any one or more of the aforementioned modes and arrangements can be modified and/or combined into one or more electrosurgical configurations to perform a device function. For example, in some medical devices, it may be desirable to combine the first arrangement 162 and the filth arrangement 170 into an electrosurgical combination to perform one or more device functions.

Figure 9:
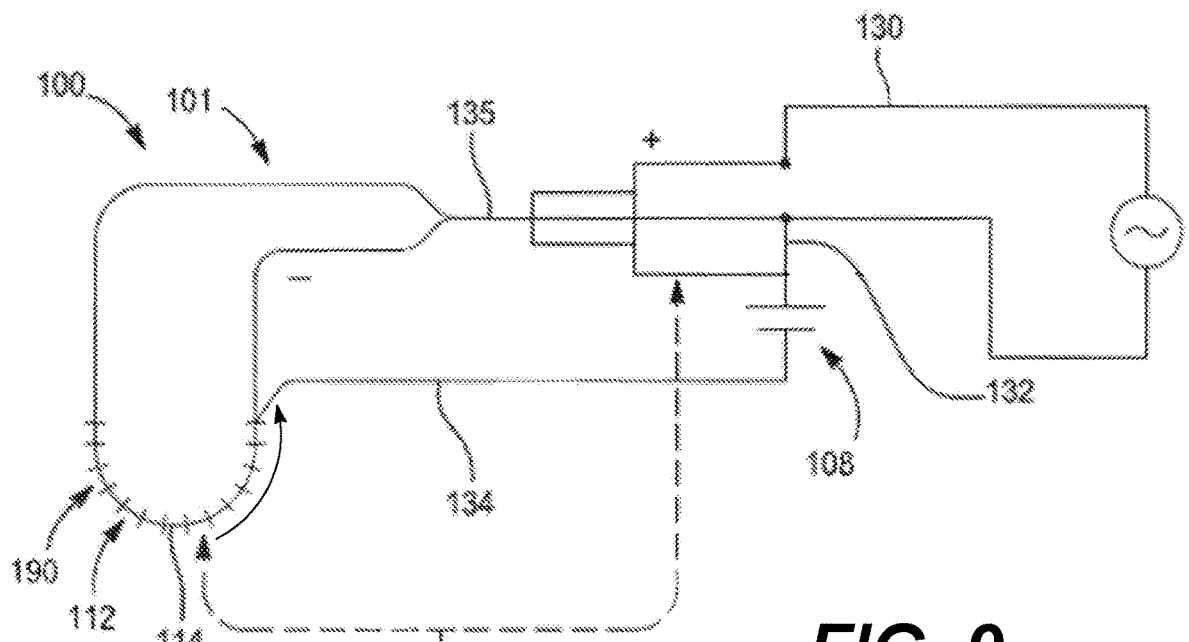
FIG. 9 is an exams to of a circuit diagram of a resectoscope loop.

FIG. 9 illustrates a schematic circuit of an electrosurgical medical device 100 that may be a resectoscope loop electrode 101. The electrosurgical medical device 100 includes a heating power supply 108 and a therapy power supply 110. The electrosurgical medical device 100 includes a first electrode 112 that may be a loop electrode 190. The first electrode 112 includes a heater 114.

A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection or conductor wire 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. An ablation path 192 extends from the first electrode 112, the heater 114, or both to the heating power connection 132.

Figure 10:
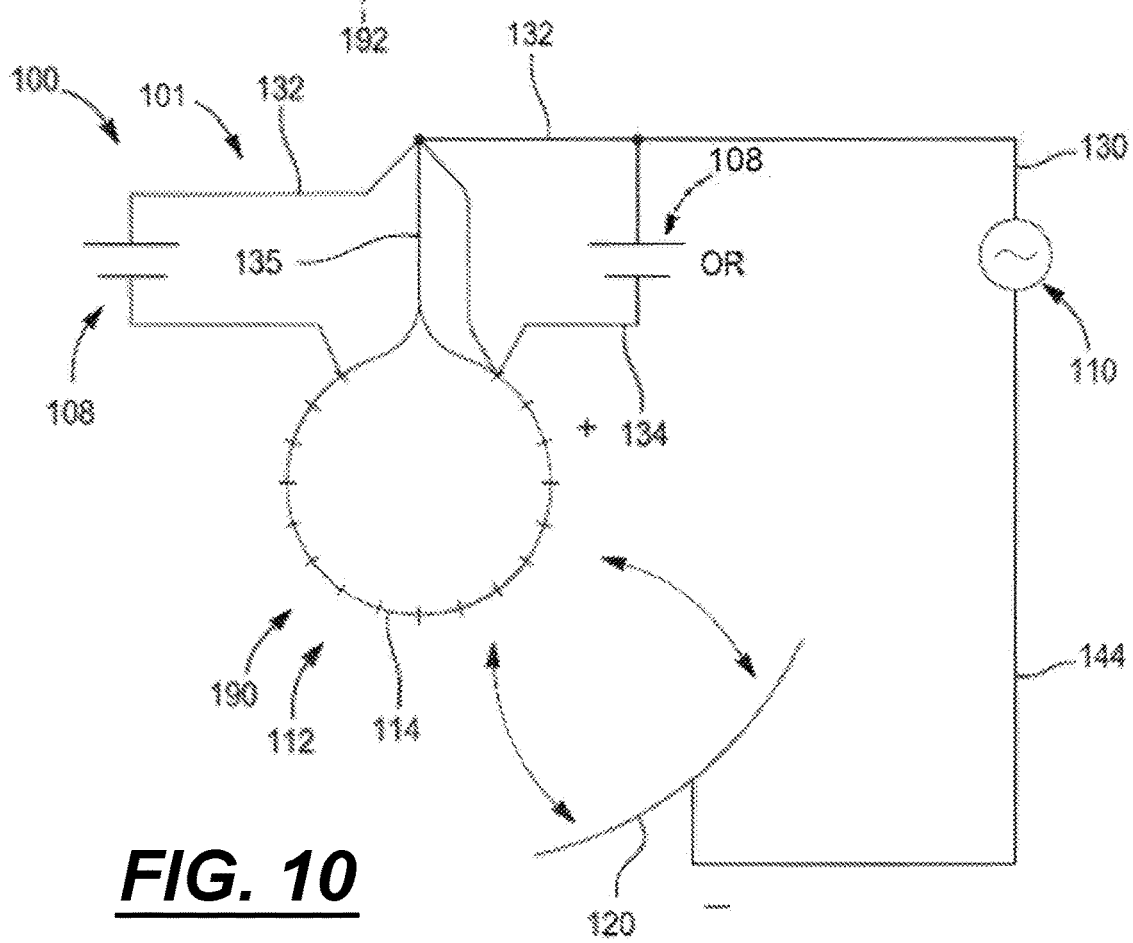
FIG. 10 is a circuit diagram of a monopolar snare.

FIG. 10 illustrates a schematic circuit of an electrosurgical medical device 100 that may be a monopolar snare 101. The electrosurgical medical device 100 includes a heating power supply 108 and a therapy power supply 110. The heating power supply 108 can be located in one or both of the areas shown in FIG. 10. The electrosurgical medical device 100 includes a first electrode 112 that may be a bop electrode 190. The first electrode 112 includes a heater 114. A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection or conductor wire 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. A patient pad connection 144 extends between the therapy power supply 110 and the remote or patient pad 120.

Figure 11A:
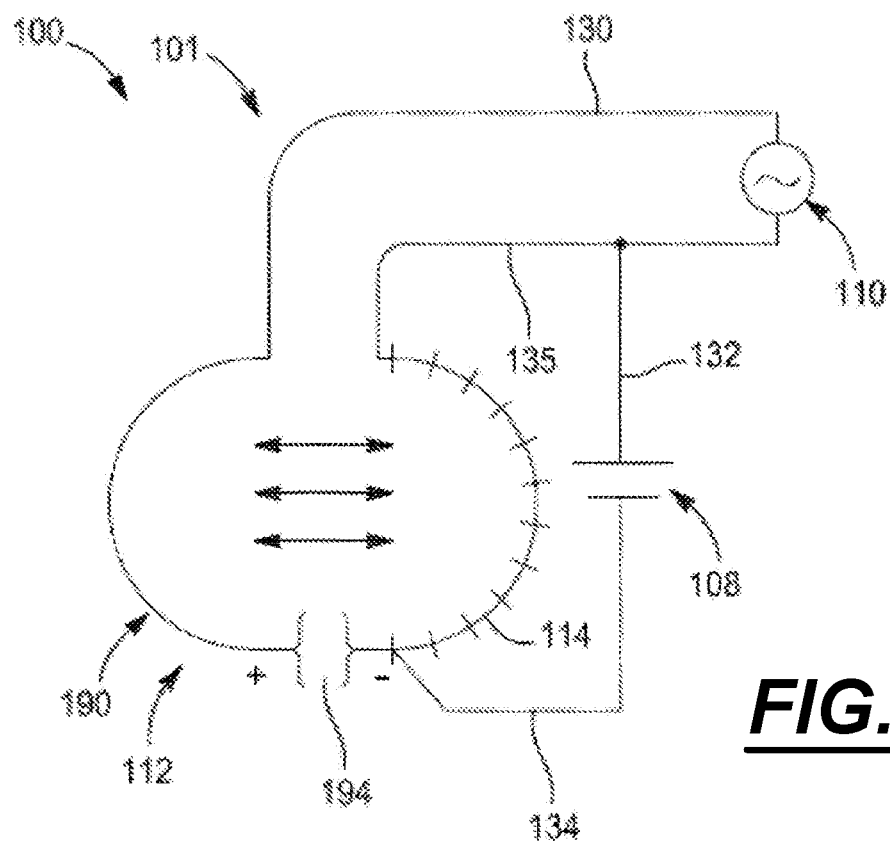
FIG. 11a is a circuit diagram of a bipolar snare.

FIG. 11a illustrates a schematic circuit of an electrosurgical medical device 100 that may be a bipolar snare 101. The electrosurgical medical device 100 includes a heating power supply 108 and a therapy power supply 110. The electrosurgical medical device 100 includes a first electrode 112 that may be a loop electrode 190. The first electrode 112 includes a heater 114. A therapeutic power connection 130 extends between the therapy power supply 110 and the first electrode 112, which provides therapeutic power to the first electrode 112. A heating power connection 132 extends between the heating power supply 108 and the heater 114 of the first electrode 112. The heating power connection 132 and the therapeutic power connection 130 can be a single, common connection 135 carrying two signals from the heating power supply 108 and the therapy power supply 110. That is, the connection 135 can carry therapeutic power to the first electrode 112 and heating power to the heater 114. A second heating power connection 134 extends between the heating power supply 108 and the first electrode 112. At the distal end of the electrosurgical medical device 100 is a non-conductive joint 194, so there is no necessity for a conductive break at a proximal end of the loop electrode 190.

Figure 11B:
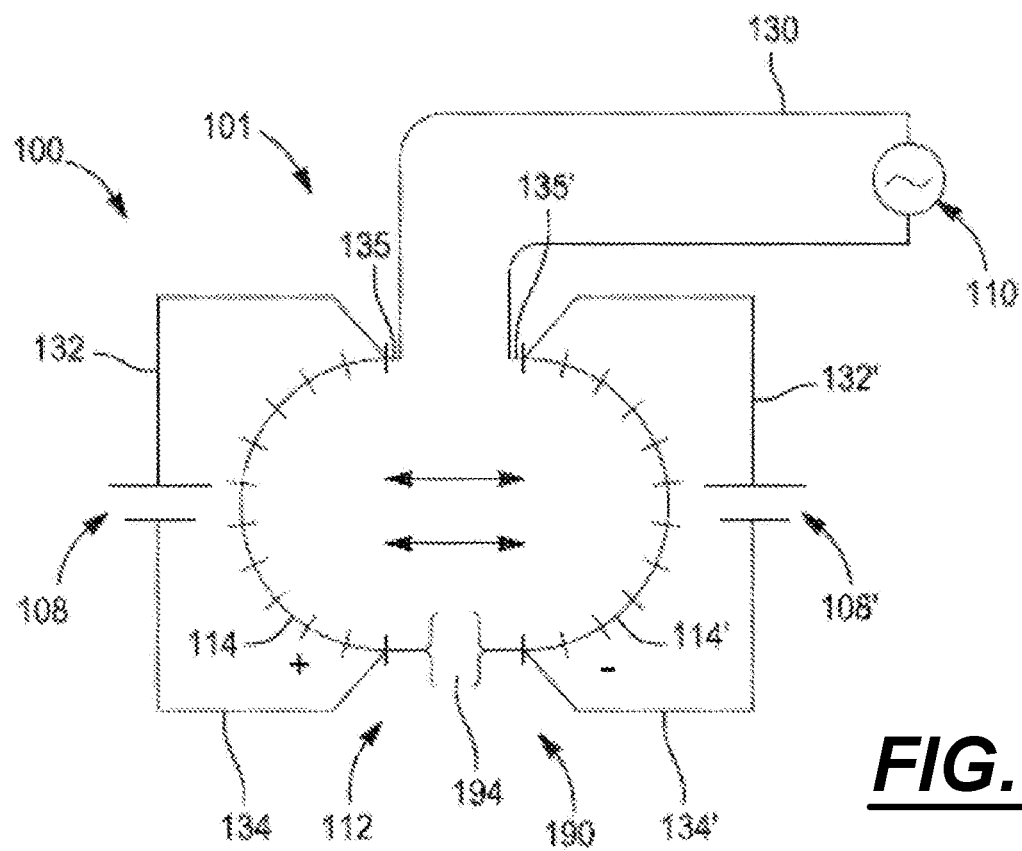
FIG. 11b is a circuit diagram of a bipolar snare.

FIG. 11b illustrates a schematic circuit of an electrosurgical medical device 100 that may be a bipolar snare 101. The electrosurgical medical device 100 includes one or both heating power supplies 108, 108' as shown, and a therapy power supply 110. The electrosurgical medical device 100 includes a first electrode 112 that may be a loop electrode 190. The first electrode 112 includes one or both heaters 114, 114' shown that are in communication with corresponding power supplies 108, 108'. A therapeutic power connection 130 extends between the therapy power supply 110 and the first electrode 112, which provides therapeutic power to the first electrode 112. A heating power connection 132, 132' extends between the corresponding heating power supply 108, 108' and the corresponding heater 114, 114' of the first electrode 112. At the distal end of the electrosurgical medical device 100 is a non-conductive joint 194, so there is no necessity for a conductive break at a proximal end of the loop electrode 190.

The heating power connection 132 or 132' and the therapeutic power connection 130 can be a single, commit connection 135 135' carrying two signal from the heating power supply 108 and the therapy power supply 110. That is, the connection 135, 135' can carry therapeutic power to the first electrode 112 and heating power to the heater 114, 114'. A second heating power connection 134, 134' extends between the heating power supply 108, 108' and the first electrode 112.

Figure 12:
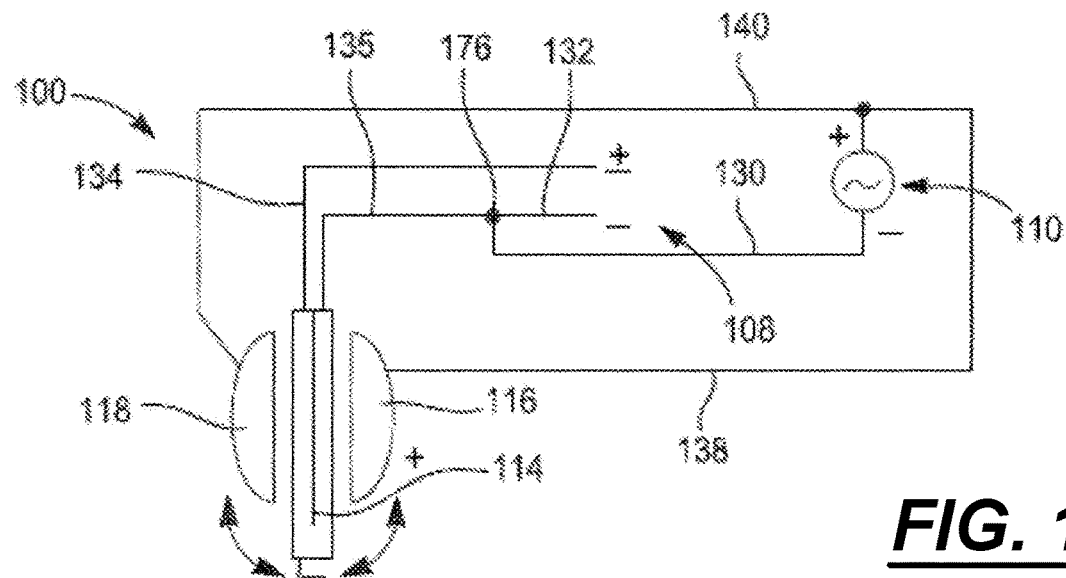
FIG. 12 is a schematic of a circuit of a medical device.

FIG. 12 illustrates a schematic circuit of an electrosurgical medical device 100. The electrosurgical medical device 100 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114.

A therapeutic power connection or conductor wire 130 extends between the therapy power supply 110 and the first electrode 112. The therapy power supply 110 provides therapeutic power to the first electrode 112 via the conductor wire 130.

A therapeutic power connection or conductor wire 138 extends between the therapy power supply 110 and the second electrode 116. The therapy power supply 110 provides therapeutic power to the second electrode 116 via the conductor wire 138.

A therapeutic power connection or conductor wire 140 extends between the therapy power supply 110 and the third electrode 118. The therapy power supply 110 provides therapeutic power to the third electrode 118 via the conductor wire 140.

Heating power connection or conductor wires 132, 134 extend between the heating power supply 108 and the heater 114. Heating power is provided from the heating power supply 108 to the heater 114 via the conductor wires 132, 134.

The heating power connection or conductor wire 132 and the therapeutic power connection or conductor wire 130 can be electrically connected or joined at a node 176. A single power connection or conductor wire 135 extends from the connection or node 176 to the heater 114. The single conductor wire 135 is thus adapted to carry a heating signal from the heating power supply 108 to the heater 114 and a therapy signal from the therapy power supply 110 to the electrode 112. Of course, another node or connection extends proximate to the electrode 112 and heater 114 where the single conductor wire 135 branches to connect the single conductor wire 135 to each of the heater 114 and electrode 112.

During use, therapeutic power can be communicated from the therapy power supply 110 to the first electrode 112 and communicated back to the therapy power supply 110 via the second electrode 116, the third electrode 118, or both (i.e., bipolar mode).

During use, therapeutic power can be communicated from the therapy power supply 110 to the third electrode 118 and back to the therapy power supply 110 via the second electrode 116 (bipolar triode). While the therapeutic power is communicated between the second and third electrodes 116, 118, the therapeutic power, the heating power, or both can be provided to the first electrode 112. Alternatively, the supply of heating power to the heater 114 can be prevented while therapeutic power is being communicated between the second and third electrodes 116, 118. Moreover, the supply of therapeutic power to the first electrode 112 can be prevented while therapeutic power being communicated between the second and third electrodes 116, 118.

Figure 13:
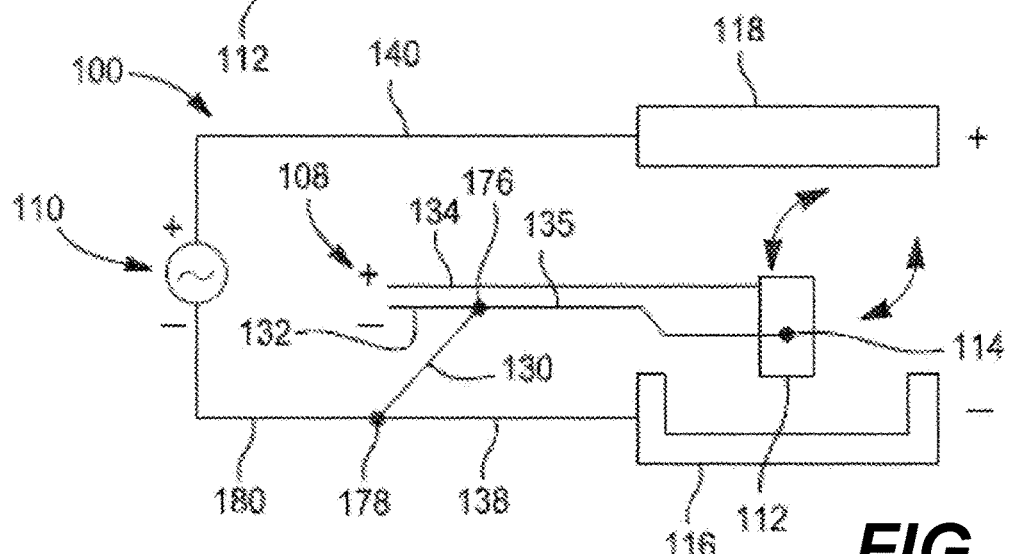
FIG. 13 is a schematic of a circuit of a medical device.

FIG. 13 illustrates a schematic circuit of an electrosurgical medical device 100. The electrosurgical medical device 100 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114.

A therapeutic power connection or conductor wire 180 extends between the therapy power supply 110 and a node or connection 178. From the node or connection 178, a therapeutic power connection or conductor wire 130 extends to the first electrode 112. From the node or connection 178, a therapeutic power connection or conductor wire 138 extends between to the second electrode 116. The therapy power supply 110 provides therapeutic power to the first electrode 112 and the second electrode 116 via the corresponding conductor wires 180, 130, 138.

A therapeutic power connection or conductor wire 140 extends between the therapy power supply 110 and the third electrode 118. The therapy power supply 110 provides therapeutic power to the third electrode 118 via the conductor wire 140.

Heating power connection or conductor wires 132, 134 extend between the heating power supply 108 and the heater 114. Heating power is provided from the heating power supply 108 to the heater 114 via the conductor wires 132, 134.

The heating power connection or conductor wire 132 and the therapeutic power connection or conductor wire 130 can be electrically connected or joined at a node 176. A single power connection or conductor wire 135 extends from the connection or node 176 to the heater 114. The single conductor wire 135 is thus adapted to carry a heating signal from the heating power supply 108 to the heater 114 and a therapy signal from the therapy power supply 110 to the electrode 112. Another node or connection or branch is located proximate to the electrode 112 and heater 114 where the single conductor wire 135 branches to connect the single conductor wire 135 to each of the heater 114 and electrode 112.

During use, therapeutic power can be communicated from the therapy power supply 110 to the first electrode 112 and communicated back to the therapy power supply 110 via the third electrode 118 (i.e., bipolar mode).

During use, therapeutic power can be communicated from the therapy power supply 110 to the third electrode 118 and back to the therapy power supply 110 via the second electrode 116 (bipolar mode). While the therapeutic power is communicated between the second and third electrodes 116, 118, the therapeutic power, the heating power, or both can be provided to the first electrode 112. Alternatively, the supply of heating power to the heater 114 can be prevented while therapeutic power is being communicated between the second and third electrodes 116, 118. Moreover, the supply of therapeutic power to the first electrode 112 can be prevented while therapeutic power is being communicated between the second and third electrodes 116, 118.

Figure 14:
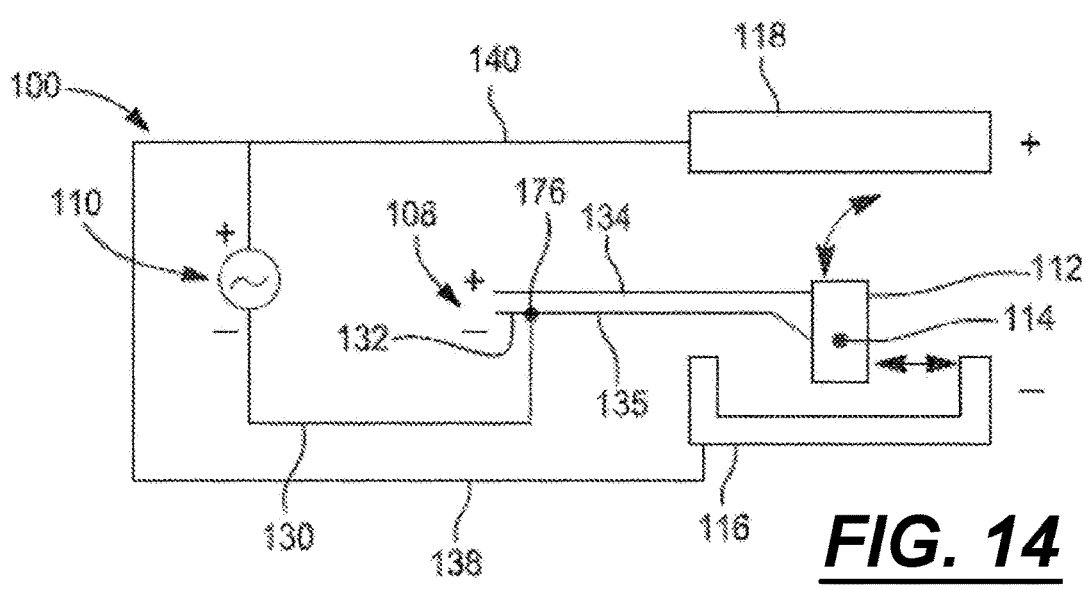
FIG. 14 is a schematic of a circuit of a medical device.

FIG. 14 illustrates a schematic circuit of an electrosurgical medical device 100. The electrosurgical medical device 100 includes a heating power supply 108 and a therapy power supply 110. The heating power supply 108 provides heating power to the electrosurgical medical device 100, and the therapy power supply 110 provides therapeutic power to the electrosurgical medical device 100. The electrosurgical medical device 100 includes a first electrode 112, a second electrode 116, and a third electrode 118. The first electrode 112 includes a heater 114.

A therapeutic power connection or conductor wire 130 extends between the therapy power supply 110 and the first electrode 112. The therapy power supply 110 provides therapeutic power to the first electrode 112 via the conductor wire 130.

A therapeutic power connection or conductor wire 138 extends between the therapy power supply 110 and the second electrode 116. The therapy power supply 110 provides therapeutic power to the second electrode 116 via the conductor wire 138.

A therapeutic power connection or conductor wire 140 extends between the therapy power supply 110 and the third electrode 118. The therapy power supply 110 provides therapeutic power to the third electrode 118 via the conductor wire 140.

Heating power connection or conductor wires 132, 134 extend between the heating power supply 108 and the heater 114. Heating power is provided from the heating power supply 108 to the heater 114 via the conductor wires 132, 134.

The heating power connection or conductor wire 132 and the therapeutic power connection or conductor wire 130 are electrically connected or joined together at a node 176. A single power connection or conductor wire 135 extends from the connection or node 176 to the heater 114. The single conductor wire 135 is thus adapted to carry a heating signal from the heating power supply 108 to the heater 114 and a therapy signal from the therapy power supply 110 to the electrode 112. Of course, another node or connection extends proximate to the electrode 112 and heater 114 where the single conductor wire 135 branches to connect the single conductor wire 135 to each of the heater 114 and electrode 112.

During use, therapeutic power can be communicated from the therapy power supply 110 to the first electrode 112 and communicated back to the therapy power supply 110 via the second electrode 116, the third electrode 118, or both (i.e., bipolar mode).

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

By use of the term "may" herein, it is intended that any described attributes that "may" be included are optional.

While the terms first, second, third, etc., may be used herein to describe various elements, components regions, layers and/or sections, these elements, components, regions, layers and/or sections should not be limited by these terms. These terms may be used to distinguish one element, component, region, layer or section from another region, layer or section. Terms such as "first," "second," and other numerical tem when used herein do not imply a sequence or order unless clearly indicated by the context. Thus, a first element, component, region, layer or section discussed, below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device; comprising:
   i. a hand piece comprising a first electrode including a heater, and
   ii. a heating power supply selectively providing heating power to the heater; and
   iii. a therapy power supply selectively providing therapeutic power to the first electrode,
   wherein the medical device is changeable between operating a first electrosurgical configuration and a second electrosurgical configuration,
   wherein in the first electrosurgical configuration, the heating power supply provides the heating power to the heater to heat the first electrode and the therapy power supply provides the therapeutic power to the first electrode,
   wherein a single conductor line carries the heating power to the heater and the therapeutic power to the first electrode,
   wherein in the first electrosurgical configuration, the first electrode is in communication with a remote electrode,
   wherein in the first electrosurgical configuration, the medical device operates in a monopolar mode,
   wherein the first electrode is in communication with a first extension,
   wherein in the first electrosurgical configuration, the first extension member is a heated monopolar blade, and
   wherein the first extension member is moveable relative to any other extensions.

2. The medical device of claim 1, wherein the hand piece comprises a second electrode.

3. The medical device of claim 2, wherein the second electrode is in communication with a second extension.

4. The medical device of claim 3, wherein the heater is electrically connected to the heating power supply by a first conductive path comprising a first connection and a second connection,
   wherein the first electrode electrically connected to the therapy power supply by a second conductive path comprising a third connection, and
   wherein the first connection and third connection are a single, electrically connected connection providing the heating power to the heater and the therapeutic power to the first electrode.

5. The medical device of claim 1, wherein the hand piece comprises a second electrode and a third electrode,
   wherein in the second electrosurgical configuration, the second electrode is in communication with the therapy power supply and is also in communication with the first electrode, the third electrode, or both, and
   wherein in the second electrosurgical configuration; the medical device operates in a bipolar mode.

6. The medical device of claim 1, wherein the first electrode is operable in both the first electrosurgical configuration and the second electrosurgical configuration.

7. The medical device of claim 6, wherein the hand piece comprises a second electrode,
   wherein in the second electrosurgical configuration, the first electrode is in communication with the second electrode and the therapy power supply,
   wherein in the second electrosurgical configuration, the medical device operates in a bipolar mode, and
   wherein in the second electrosurgical configuration, the heating power supply selectively provides heating power to the heater.

8. The medical device of claim 7, wherein the medical device includes a third electrode,
   wherein the third electrode is in communication with at least one of the first and second electrodes in the second electrosurgical configuration, wherein in the second electrosurgical configuration, the medical device operates in a bipolar mode.

9. A medical device, comprising:
i. a hand piece comprising:
a. a first electrode including a heater,
b. a second electrode, and
c. a third electrode;
ii. a heating power supply selectively supplying heating power to the heater; and
iii. a therapy power supply selectively providing therapeutic power to the first, second, and/or third electrodes,
wherein the medical device is selectively changeable between a first electrosurgical configuration and a second electrosurgical configuration,
wherein in the first electrosurgical configuration, the heating power supply provides the heating power to the heater to heat the first electrode and the therapy power supply provides the therapeutic power to the first electrode,
wherein the first electrode is in communication with a first extension, the second electrode is in communication with a second extension, and the third electrode is in communication with a third extension,
wherein in the first electrosurgical configuration, the first extension member is a heated blade,
wherein in the second electrosurgical configuration, the therapy power supply provides therapeutic power to the second and third electrodes so that the medical device operates in a bipolar mode, and
wherein the second and third extensions comprise opposing jaws of a forceps device.

10. A medical device, comprising:
i. a hand piece comprising a first electrode including a heater, and
ii. a heating power supply selectively providing heating power to the heater; and
iii. a therapy power supply selectively providing therapeutic power to the first electrode,
wherein the medical device is changeable between operating a first electrosurgical configuration and a second electrosurgical configuration,
wherein in the first electrosurgical configuration, the heating power supply provides the heating power to the heater to heat the first electrode and the therapy power supply provides the therapeutic power to the first electrode,
wherein a single conductor line carries the heating power to the heater and the therapeutic power to the first electrode,
wherein the hand piece comprises a second electrode and a third electrode,
wherein in the second electrosurgical configuration, the second electrode is in communication with the therapy power supply and is also in communication with the first electrode, the third electrode, or both,
wherein in the second electrosurgical configuration, the medical device operates in a bipolar mode,
wherein the first electrode is in communication with a first extension, the second electrode is in communication with a second extension, and the third electrode is in communication with a third extension,
wherein in the first electrosurgical configuration, the first extension member is a heated blade, and
wherein in the second electrosurgical configuration the second and third extensions comprise opposing jaws of a forceps device.

11. The medical device of claim 10, wherein the medical device selectively operates in the first and second electrosurgical configuration.

12. The medical device of claim 10, wherein the heater is electrically connected to the heating power supply by a first conductive path comprising a first connection and a second connection,
wherein the first electrode is electrically connected to the therapy power supply by a second conductive path comprising a third connector, and
wherein the first connection and third connection are a common connection.

13. A medical device, comprising:
i. a hand piece comprising a first electrode including a heater, and
ii. a heating power supply selectively providing heating power to the heater; and
iii. a therapy power supply selectively providing therapeutic power to the first electrode,
wherein the medical device is changeable between operating a first electrosurgical configuration and a second electrosurgical configuration,
wherein in the first electrosurgical configuration, the heating power supply provides the heating power to the heater to heat the first electrode and the therapy power supply provides the therapeutic power to the first electrode,
wherein a single conductor line carries the heating power to the heater and the therapeutic power to the first electrode,
wherein the hand piece comprises a second electrode and a third electrode,
wherein in the second electrosurgical configuration, the second electrode is in communication with the therapy power supply and is also in communication with the first electrode, the third electrode, or both,
wherein in the second electrosurgical configuration, the medical device operates in a bipolar mode,
wherein the first electrode is in communication with a first extension, the second electrode is in communication with a second extension, and the third electrode is in communication with a third extension,
wherein in the first electrosurgical configuration, the first extension member is a heated blade,
wherein in the second electrosurgical configuration, the first extension comprises a centrally-located heated extension that is sandwiched between the second and third extensions, and
wherein in the second electrosurgical configuration, the medical device operates in a bipolar mode.

* * * * *

UNITED STATES PATENT AND TRADEMARK OFFICE
CERTIFICATE OF CORRECTION

PATENT NO. : 11,000,328 B2  Page 1 of 1
APPLICATION NO. : 15/797014
DATED : May 11, 2021
INVENTOR(S) : Batchelor et al.

It is certified that error appears in the above-identified patent and that said Letters Patent is hereby corrected as shown below:

In the Claims

In Column 25, Line 65, in Claim 1, delete "device;" and insert --device,-- therefor In Column 26, Line 48, in Claim 5, delete "configuration;" and insert --configuration,-- therefor In Column 28, Line 26, in Claim 13, delete "iii," and insert --iii.-- therefor Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*